(12) United States Patent
Ales, III et al.

(10) Patent No.: US 7,737,322 B2
(45) Date of Patent: Jun. 15, 2010

(54) PERSONAL CARE PRODUCTS WITH MICROCHEMICAL SENSORS FOR ODOR DETECTION

(75) Inventors: Thomas Michael Ales, III, Neenah, WI (US); Jan G. Dong, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 354 days.

(21) Appl. No.: 11/314,438

(22) Filed: Dec. 21, 2005

(65) Prior Publication Data

US 2007/0142799 A1   Jun. 21, 2007

(51) Int. Cl.
   *A61F 13/15* (2006.01)
(52) U.S. Cl. .................. 604/361; 604/366; 604/367
(58) Field of Classification Search .................. 604/361, 604/366, 367
   See application file for complete search history.

(56) References Cited

U.S. PATENT DOCUMENTS

| | | | |
|---|---|---|---|
| 4,100,324 | A | 7/1978 | Anderson et al. |
| 4,704,116 | A | 11/1987 | Enloe |
| 4,940,464 | A | 7/1990 | Van Gompel et al. |
| 5,114,781 | A | 5/1992 | Morman |
| 5,116,662 | A | 5/1992 | Morman |
| 5,284,703 | A | 2/1994 | Everhart et al. |
| 5,350,624 | A | 9/1994 | Georger et al. |
| 5,486,166 | A | 1/1996 | Bishop et al. |
| 5,490,846 | A | 2/1996 | Ellis et al. |
| 5,645,542 | A | 7/1997 | Anjur et al. |
| 5,766,389 | A | 6/1998 | Brandon et al. |
| 5,820,973 | A | 10/1998 | Dodge, II et al. |
| 5,883,028 | A | 3/1999 | Morman et al. |
| 5,964,743 | A | 10/1999 | Abuto et al. |
| 6,097,297 | A * | 8/2000 | Fard .......................... 340/604 |
| 6,231,557 | B1 | 5/2001 | Krautkramer et al. |
| 6,362,389 | B1 | 3/2002 | McDowall et al. |
| 6,372,951 | B1 | 4/2002 | Ter-Ovanesyan et al. |
| 6,384,296 | B1 | 5/2002 | Roe et al. |
| 6,395,955 | B1 | 5/2002 | Roe et al. |
| 6,407,308 | B1 | 6/2002 | Roe et al. |

(Continued)

FOREIGN PATENT DOCUMENTS

WO   00/00233 A1   1/2000

(Continued)

OTHER PUBLICATIONS

Ho, et al., "Field Demonstrations of Chemiresistor and Surface Acoustic Wave Microchemical Sensors at the Nevada Test Site," SAND 2003-0799, Mar. 2003, Sandia National Laboratories.

(Continued)

*Primary Examiner*—Jacqueline F. Stephens
(74) *Attorney, Agent, or Firm*—Armstrong Teasdale LLP

(57) ABSTRACT

Absorbent articles comprising one or more sensors capable of detecting the presence of a body waste in the absorbent article are described. In particular, the absorbent articles comprise at least one chemiresistor capable of detecting the presence of volatile organic compounds associated with a body waste. When a body waste is detected, an indicator means signals a caregiver and/or a user of the absorbent article that an insult has occurred.

28 Claims, 15 Drawing Sheets

U.S. PATENT DOCUMENTS

| | | | |
|---|---|---|---|
| 6,433,244 | B1 | 8/2002 | Roe et al. |
| 6,433,694 | B1 | 8/2002 | Dolan et al. |
| 6,552,245 | B1 | 4/2003 | Roessler et al. |
| 6,570,053 | B2 | 5/2003 | Roe et al. |
| 6,641,134 | B1 | 11/2003 | Dobbertin et al. |
| 6,645,190 | B1 | 11/2003 | Olson et al. |
| 6,832,507 | B1 * | 12/2004 | van de Berg et al. ............ 73/73 |
| 6,902,701 | B1 * | 6/2005 | Hughes et al. ................ 422/83 |
| 2002/0081397 | A1 | 6/2002 | McGill et al. |
| 2004/0078219 | A1 | 4/2004 | Kaylor et al. |
| 2004/0100376 | A1 | 5/2004 | Lye et al. |
| 2005/0263394 | A1 * | 12/2005 | Lewis et al. ............ 204/403.01 |

FOREIGN PATENT DOCUMENTS

| | | |
|---|---|---|
| WO | 00/16081 A1 | 3/2000 |
| WO | WO 00/37009 A2 | 6/2000 |
| WO | WO 03/051254 A2 | 6/2003 |

OTHER PUBLICATIONS

Ho, et al., "Review of Chemical Sensors for In-Situ Monitoring of Volatile Contaminants," SAND2001-0643, Mar. 2001, Sandia National Laboratories.

Hughes, et al., "Integrated chemiresistor array for small sensor platforms," Proceedings of the SPIE, 2000, pp. 519-529, vol. 4038, XP002413228.

International Search Report and Written Opinion from PCT/US2006/038835, dated Mar. 7, 2007.

* cited by examiner

PERSONAL CARE PRODUCTS WITH MICROCHEMICAL SENSORS FOR ODOR DETECTION

BACKGROUND OF DISCLOSURE

The present disclosure relates to absorbent articles, such as diapers, training pants, incontinence garments, and feminine hygiene products, which comprise one or more sensors capable of detecting the presence of a body waste, such as urine, feces, or menses, in the absorbent article. More particularly, the present disclosure relates to absorbent articles comprising at least one chemiresistor capable of detecting the presence of volatile organic compounds associated with body wastes. When the presence of a body waste is detected, an indicator means signals a caregiver and/or a wearer of the absorbent article that the absorbent article needs to be changed.

Disposable absorbent articles such as diapers, incontinence garments, and feminine hygiene products are widely used. Such articles are worn to catch and hold body waste, such as urine, feces, and menstrual fluid, for extended periods of time. However, body waste may be a skin irritant, in addition to being a major source of various types of bacteria. Consequently, when body waste is held in contact with skin for extended periods of time, the skin can become inflamed and irritated, and may develop, for example, skin rash (e.g., diaper rash, irritant rash, etc.) or other related conditions that may be caused by prolonged exposure to moisture, heat, irritants, enzymes, bacteria, the products of bacterial action, and/or pressure.

In addition to causing skin conditions such as skin rash, bacteria present in the waste can produce significant amounts of volatile organic compounds. Because human waste contains such a large number of bacteria which can lay next to the skin after release, these volatile organic compounds may also be a major source of irritants to the skin, and may be involved in skin irritation in the diapered and vaginal environments.

Furthermore, volatile organic compounds may be a significant source of objectionable odors. For example, some bacteria produce ammonia, mercaptans, or other odorous compounds through degradation of urine. Urine, for example, may also be used as a nutritional substrate by bacteria, resulting in growth of more bacteria and production of more ammonia in an increasing detrimental cycle.

As such, it would be beneficial for caregivers and/or wearers of absorbent articles to know when an absorbent article had been insulted with a body waste so the caregiver and/or wearer could change the absorbent article, thus reducing or eliminating the occurrence of unpleasant odor and skin irritation associated with wearing an absorbent article for an extended period of time. Thus, a need exists in the infant care, adult care, wound management, and feminine care products industries for a method of quickly and accurately identifying the presence of a body waste in an absorbent article.

SUMMARY OF THE DISCLOSURE

The present disclosure relates to absorbent articles, which comprise one or more sensors capable of detecting the presence of a body waste in the absorbent article. More particularly, the present disclosure relates to absorbent articles comprising at least one chemiresistor capable of detecting the presence of volatile organic compounds associated with a body waste. When a body waste is detected, an indicator means signals a caregiver and/or a user of the absorbent article that an insult has occurred. As a result, the wearer and/or caregiver can quickly and accurately determine when the absorbent article needs to be changed.

In one embodiment, the present disclosure is directed to an absorbent article comprising a chemiresistor disposed across a pair of spaced-apart electrodes, the chemiresistor comprising a plurality of electrically-conductive particles and a polymeric material; a microprocessor capable of detecting a change in the electrical resistance of the chemiresistor; and a means for signaling the presence of a change in the electrical resistance of the chemiresistor within the absorbent article. The resistance of the chemiresistor is capable of changing when the chemiresistor is exposed to an analyte selected from the group consisting of water vapor, a volatile organic compound present in an insult, and combinations thereof, wherein the insult is selected from the group consisting of urine, menstrual fluid, feces, blood, and combinations thereof.

In another embodiment, the present disclosure is directed to an absorbent article comprising a chemiresistor disposed across a pair of spaced-apart electrodes, the chemiresistor comprising a plurality of electrically-conductive particles and a polymeric material; a microprocessor capable of detecting a change in the electrical resistance of the chemiresistor; and a transmitter capable of sending a signal to a receiver at a location remote from the absorbent article, the receiver comprising a means for signaling the presence of a change in the electrical resistance of the chemiresistor within the absorbent article. The resistance of the chemiresistor is capable of changing when the chemiresistor is exposed to an analyte selected from the group consisting of water vapor, a volatile organic compound present in an insult, and combinations thereof, wherein the insult is selected from the group consisting of urine, menstrual fluid, feces, blood, and combinations thereof.

The present disclosure is also directed to a method of detecting the presence of an insult within an absorbent article. The method comprises providing to a wearer an absorbent article comprising a chemiresistor disposed across a pair of spaced-apart electrodes, the chemiresistor comprising a plurality of electrically-conductive particles and a polymeric material; monitoring an electrical property of the chemiresistor as the absorbent article is being worn by the wearer, wherein the resistance of the chemiresistor is capable of changing when the chemiresistor is exposed to an analyte selected from the group consisting of water vapor, a volatile organic compound present in an insult, and combinations thereof, wherein the insult is selected from the group consisting of urine, menstrual fluid, feces, blood, and combinations thereof; determining a proportional difference in the electrical property over time and providing a difference indicator value corresponding to the determined proportional difference; and comparing the difference indicator value to a difference threshold value to determine the presence of the insult and/or the water vapor in the absorbent article.

Also provided is a method of detecting the presence of an insult within an absorbent article. The method comprises providing to a wearer an absorbent article comprising a chemiresistor disposed across a pair of spaced-apart electrodes, the chemiresistor comprising a plurality of electrically-conductive particles and a polymeric material; monitoring an electrical property of the chemiresistor as the absorbent article is being worn by the wearer, wherein the resistance of the chemiresistor is capable of changing when the chemiresistor is exposed to an analyte selected from the group consisting of water vapor, a volatile organic compound present in an insult, and combinations thereof, wherein the insult is selected from the group consisting of urine, menstrual fluid, feces, blood, and combinations thereof; determining a rate of change in the electrical property over time and providing a rate indicator value corresponding to the determined rate of change; and comparing the rate indicator value to a rate threshold value to determine the presence of the insult and/or the water vapor in the absorbent article.

BRIEF DESCRIPTION OF THE DRAWINGS

Corresponding reference characters indicate corresponding parts throughout the drawings.

DETAILED DESCRIPTION OF THE PREFERRED EMBODIMENTS

The present disclosure relates to absorbent articles, which comprise one or more sensors capable of detecting the presence of a body waste or exudate, such as urine, feces, menses, and/or blood, in the absorbent article. The absorbent articles comprise at least one chemiresistor capable of detecting the presence of volatile organic compounds associated with body wastes. When a body waste is detected, an indicator means signals a caregiver and/or a wearer of the absorbent article that an insult has occurred. As a result, the wearer and/or caregiver can quickly and accurately determine when an insult occurs.

The present disclosure is discussed primarily in combination with children's toilet training pants. However, it will be readily apparent to one skilled in the art based on the disclosure that the chemiresistors described herein can also be used in combination with numerous other absorbent articles. As used herein, the phrase "absorbent article" generally refers to devices which absorb and contain body fluids, and more specifically, refers to devices which are placed against or near the skin to absorb and contain the various fluids discharged from the body. Examples of other absorbent articles include absorbent articles intended for personal wear, such as diapers; incontinence products; medical garments; feminine hygiene products, such as feminine napkins, panty liners, tampons, and interlabial pads; wound management products; surgical pads and bandages; other personal or healthcare garments; and the like.

Figure 1:
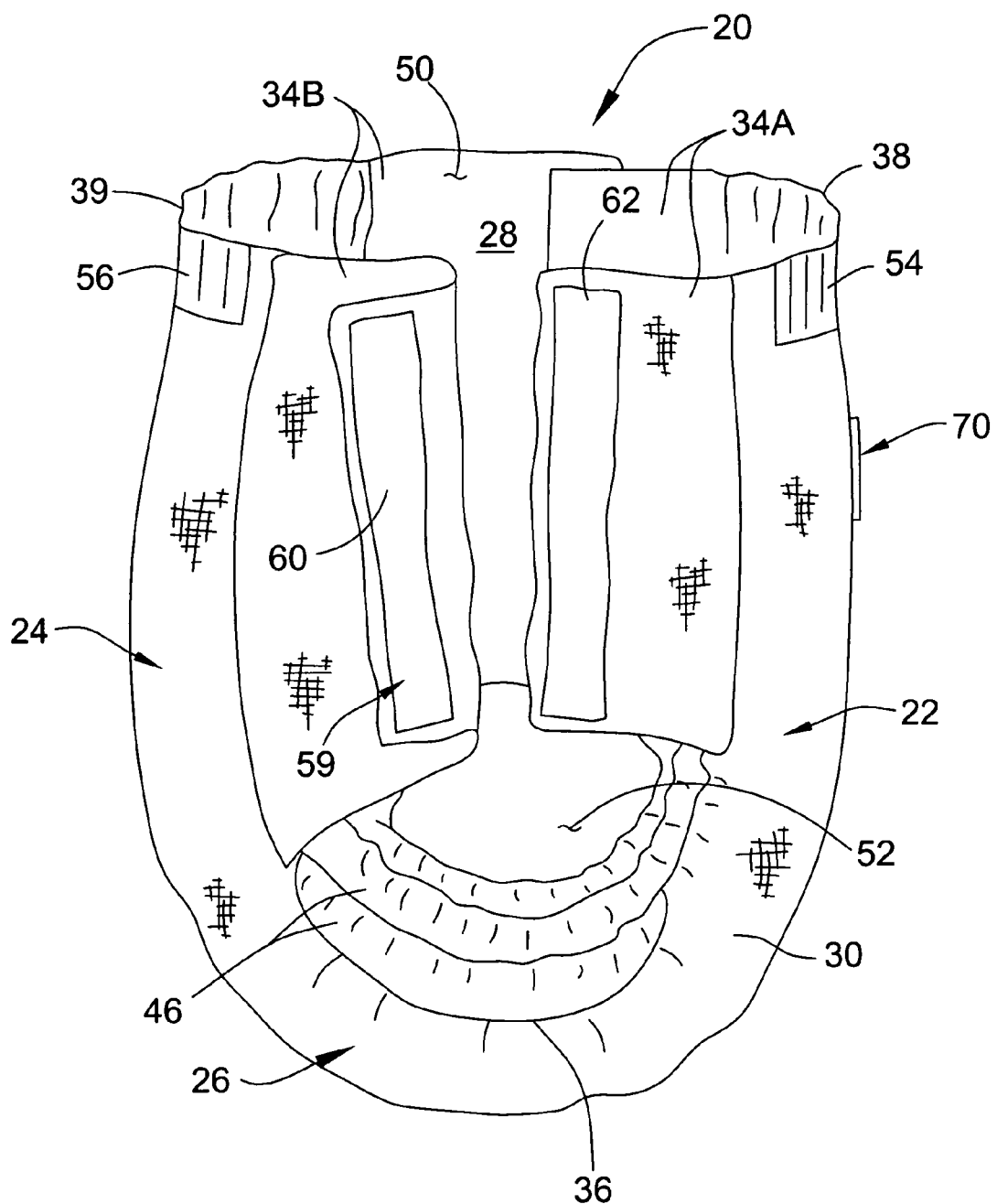
FIG. 1 is a side perspective of an absorbent article of the present disclosure shown in the form of a pair of training pants having a mechanical fastening system fastened on one side of the training pants and unfastened on the opposite side thereof.

Referring now to the drawings and in particular to FIG. 1, an absorbent article of the present disclosure is representatively illustrated therein in the form of children's toilet training pants and is indicated in its entirety by the reference numeral 20. The absorbent article 20 may or may not be disposable, which refers to articles that are intended to be discarded after a limited period of use instead of being laundered or otherwise conditioned for reuse.

By way of illustration only, various materials and methods for constructing training pants such as the pants 20 of the various aspects of the present disclosure are disclosed in PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference.

Figure 4:
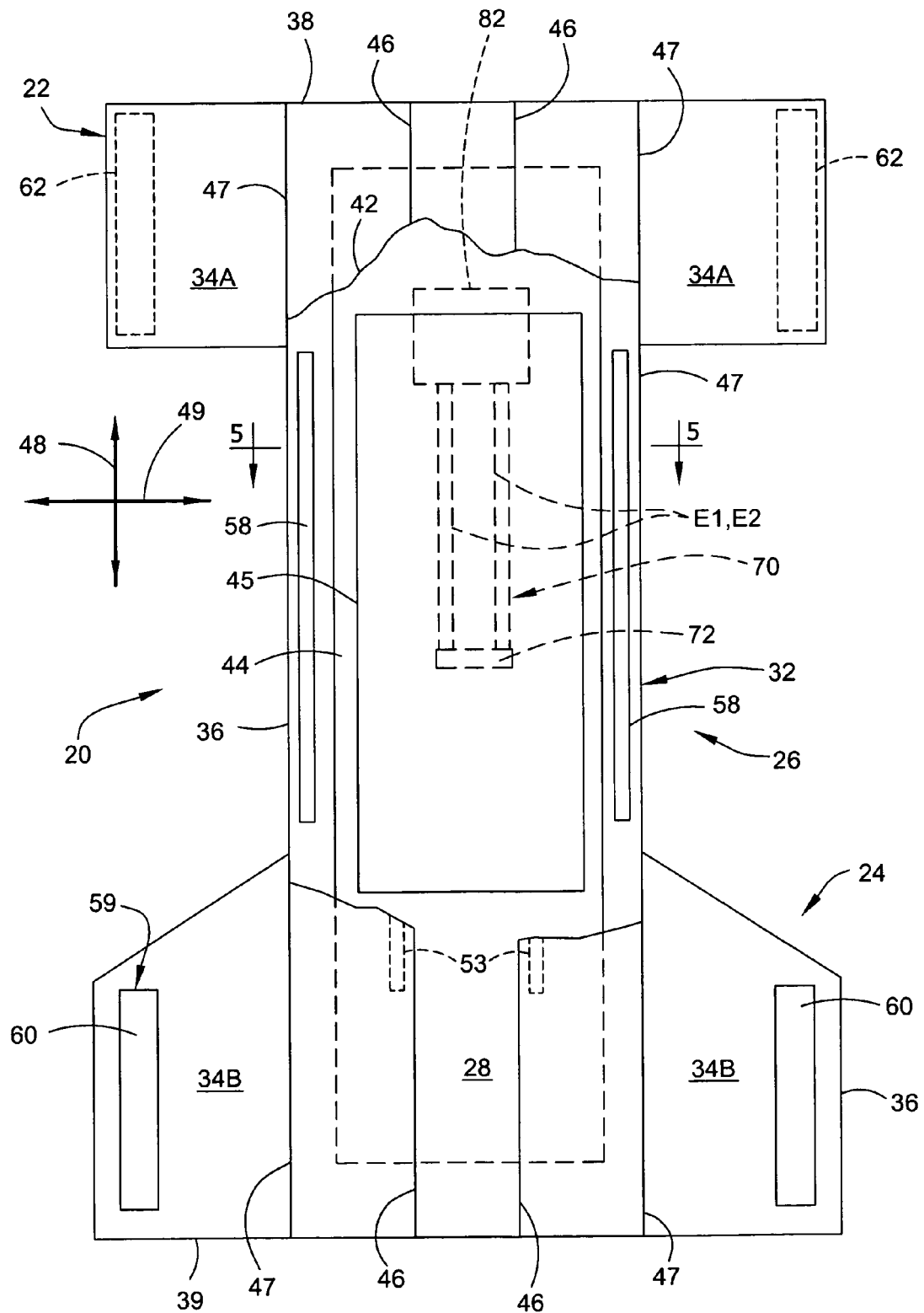
FIG. 4 is a top plan view of the training pants of FIG. 1 with the pants in an unfastened, unfolded and laid flat condition, and showing the surface of the training pants that that faces the wearer when worn and with portions cut away to show underlying features.

The pair of training pants 20 is illustrated in FIG. 1 in a partially fastened condition. The pants 20 define a longitudinal direction 48 of the pants and a lateral direction 49 thereof perpendicular to the longitudinal direction as shown in FIG. 4. The pants 20 further define a pair of longitudinal end regions, otherwise referred to herein as a front waist region, generally indicated at 22, and a back waist region, generally indicated at 24, and a center region, otherwise referred to herein as a crotch region, generally indicated at 26, extending longitudinally between and interconnecting the front and back waist regions 22, 24. The front and back waist regions 22, 24 comprise those portions of the pants 20, which when worn, wholly or partially cover or encircle the waist or mid-lower torso of the wearer. The crotch region 26 generally is that portion of the pants 20 which, when worn, is positioned between the legs of the wearer and covers the lower torso and crotch of the wearer. The pants 20 also define an inner surface 28 that faces toward the wearer when the pants are being worn, and an outer surface 30 opposite the inner surface. With additional reference to FIG. 4, the pair of training pants 20 has a pair of laterally opposite side edges 36 and a pair of longitudinally opposite waist edges (broadly, longitudinal ends), respectively designated front waist edge 38 and back waist edge 39.

In the embodiment of FIGS. 1-4, the training pants 20 comprise a generally rectangular central absorbent assembly, generally indicated at 32, and side panels 34A, 34B formed separately from and secured to the central absorbent assembly. The side panels 34A, 34B are permanently bonded along seams to the central absorbent assembly 32 in the respective front and back waist regions 22 and 24 of the pants 20. More particularly, the front side panels 34A can be permanently bonded to and extend transversely outward beyond side margins 47 of the absorbent assembly 32 at the front waist region 22, and the back side panels 34B can be permanently bonded to and extend transversely outward beyond the side margins of the absorbent assembly at the back waist region 24. The side panels 34A and 34B may be bonded to the absorbent assembly 32 using attachment means known to those skilled in the art such as adhesive, thermal or ultrasonic bonding.

The front and back side panels 34A and 34B, upon wearing of the pants 20, thus comprise the portions of the training pants 20 which are positioned on the hips of the wearer. The front and back side panels 34A and 34B can be permanently bonded together to form the three-dimensional configuration of the pants 20, or be releasably connected with one another such as by a fastening system 59 of the illustrated aspects. As is known in the art, the side panels 34A, 34B may comprise elastic material or stretchable but inelastic materials.

Figure 2:
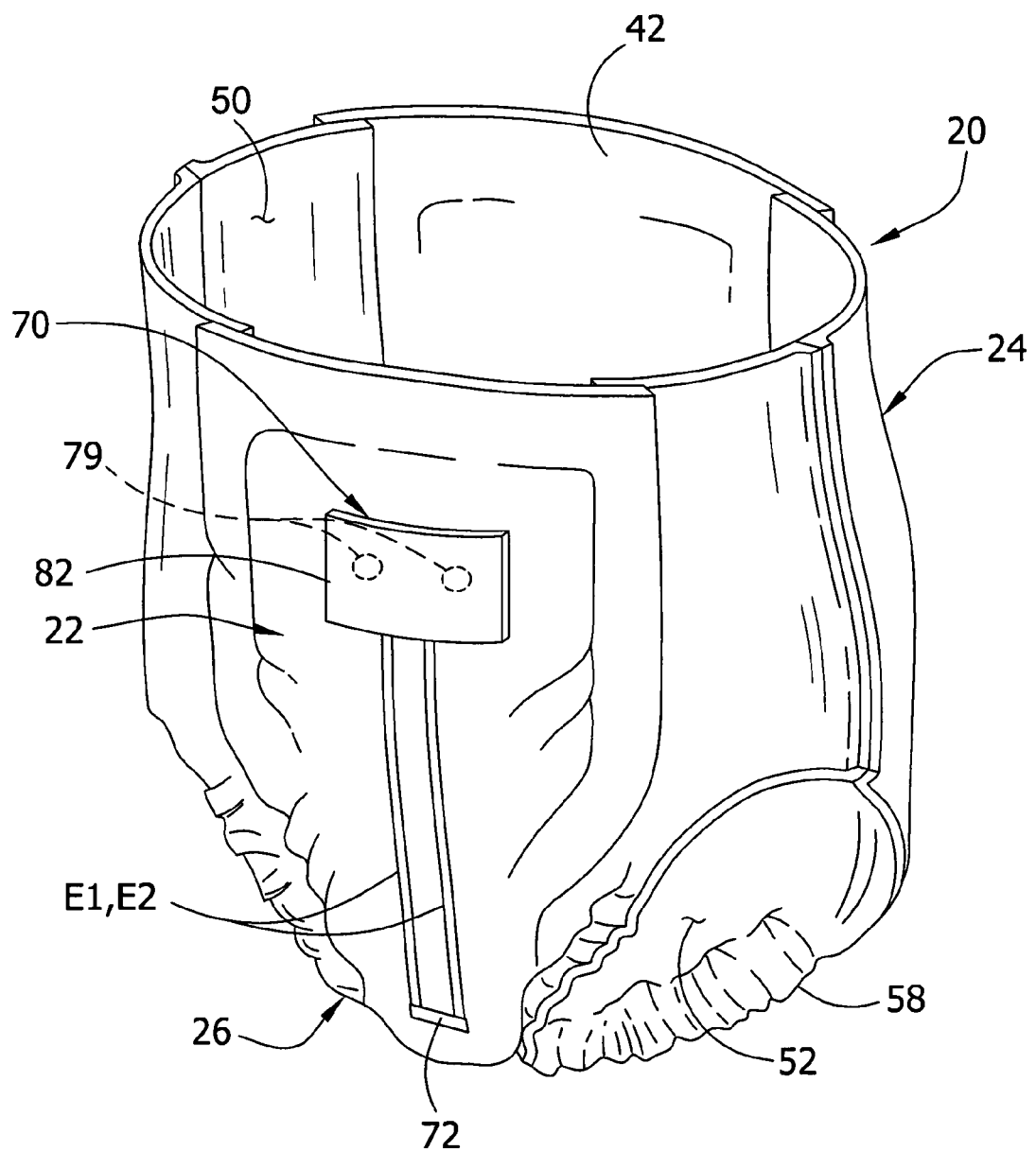
FIG. 2 is a perspective view of the pants of FIG. 1.
Figure 3:
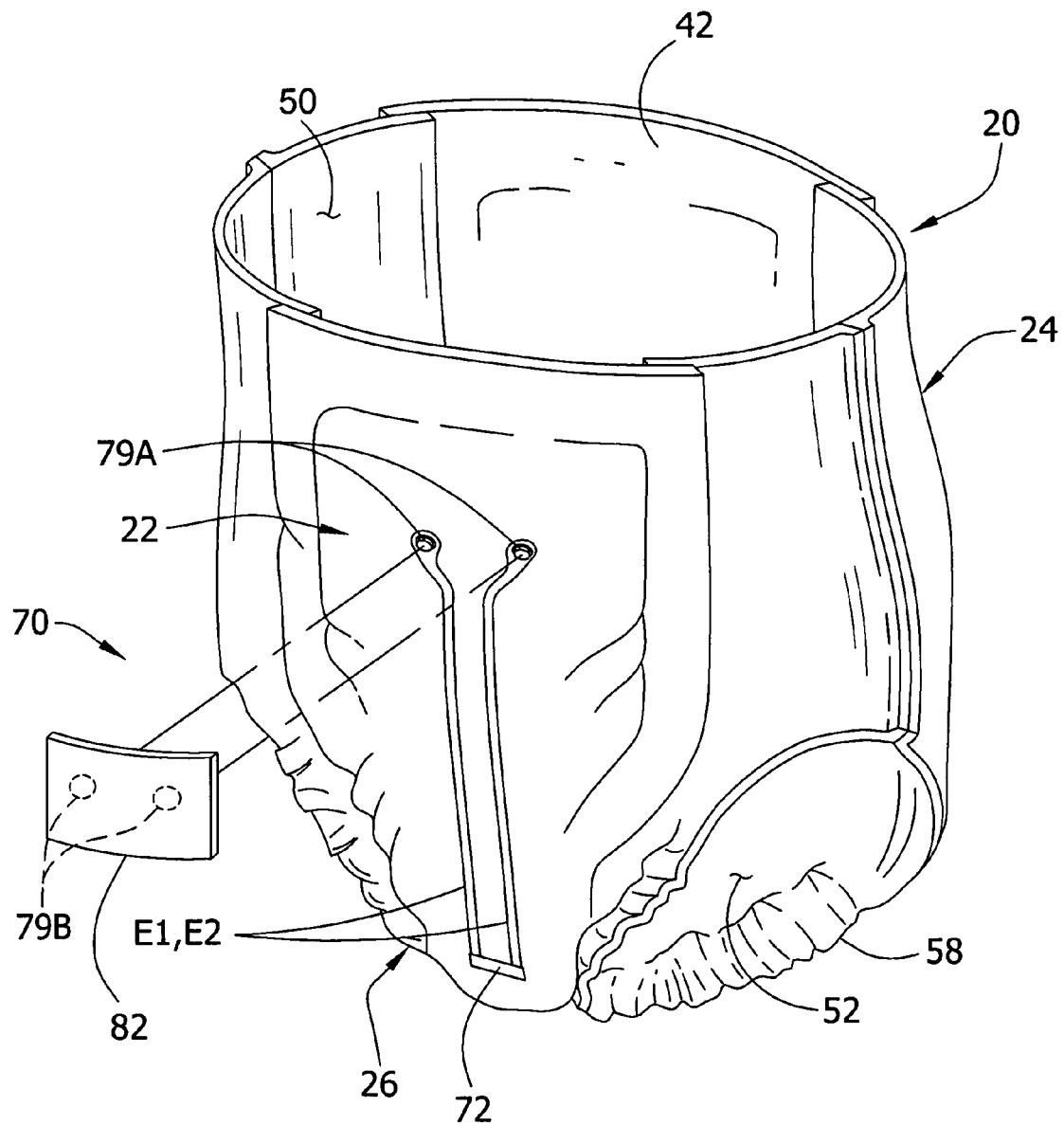
FIG. 3 is a perspective view of the pants similar to FIG. 2 showing a housing of a monitoring system removed from the article.

The absorbent assembly 32 is illustrated in FIGS. 1-3 as having a rectangular shape. However, it is contemplated that the absorbent assembly 32 may have other shapes (e.g., hourglass, T-shaped, I-shaped, and the like) without departing from the scope of this disclosure. It is also understood that the side panels 34A, 34B may instead be formed integrally with the absorbent assembly 32 without departing from the scope of this disclosure.

Figure 5:
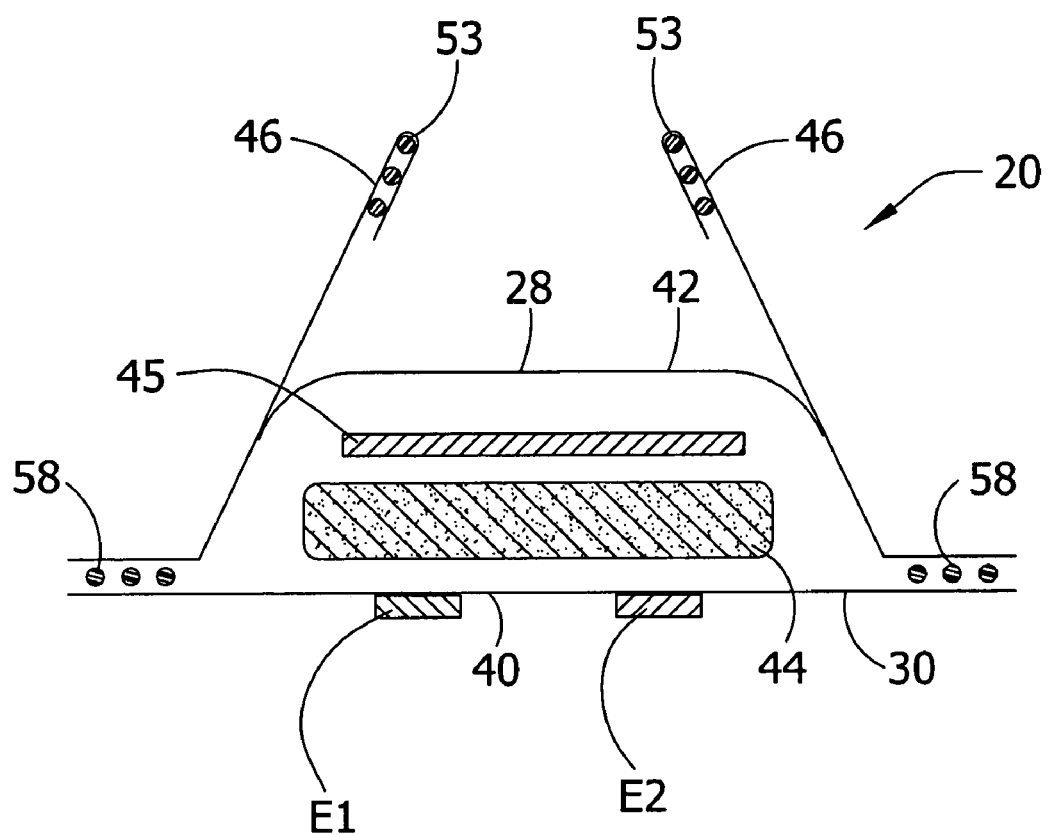
FIG. 5 is cross-sectional view of the pants taken along the plane including line 5-5 of FIG. 4.

As shown best in FIGS. 4 and 5, the absorbent assembly 32 comprises an outer cover 40 and a bodyside liner 42 attached to the outer cover 40 in a superposed (opposed) relation therewith by adhesives, ultrasonic bonds, thermal bonds, pressure bonds, or other conventional techniques. The liner 42 is suitably joined to the outer cover 40 along at least a portion of the longitudinal ends of the pants 20. In addition, the liner 42 is suitably joined to the outer cover 40. The liner 42 is suitably adapted, i.e., positioned relative to the other components of the pants 20, for contiguous relationship with the wearer's skin during wear of the pants. The absorbent assembly 32 also comprises an absorbent structure 44 disposed between the outer cover 40 and the bodyside liner 42 for absorbing liquid body exudates exuded by the wearer and a surge management layer 45 disposed between the absorbent structure and the bodyside liner. A pair of containment flaps 46 is secured to the bodyside liner 42 for inhibiting the lateral flow of body exudates.

With the training pants 20 in the fastened position as partially illustrated in FIG. 1, the front and back waist regions are connected together by the fastening system 59 to define the three-dimensional pants configuration having a waist opening 50 and a pair of leg openings 52. The front and back waist edges 38 and 39 (e.g., longitudinal ends) of the training pants 20 are configured to encircle the waist of the wearer to define the waist opening 50 (FIG. 1) of the pants.

As illustrated in FIG. 4, a flap elastic member 53 can be operatively joined with each containment flap 46 in any suitable manner as is well known in the art. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pants 20 may comprise a front waist elastic member 54 (FIG. 1), a rear waist elastic member 56, and leg elastic members 58 (FIGS. 2-4), as are known to those skilled in the art. The flap elastic members 53, the waist elastic members 54 and 56, and the leg elastic members 58 can be formed of any suitable elastic material that is well known to those skilled in the art.

The fastening system 59 of the illustrated embodiment comprises laterally opposite first fastening components 60 adapted for refastenable engagement to corresponding laterally opposite second fastening components 62. In one embodiment, a front or outer surface of each of the fastening components 60, 62 comprises a plurality of engaging elements. The engaging elements of the first fastening components 60 are adapted to repeatedly engage and disengage corresponding engaging elements of the second fastening components 62 to releasably secure the pants 20 in its three-dimensional configuration. The fastening components 60, 62 can comprise any refastenable fasteners suitable for absorbent articles, such as adhesive fasteners, cohesive fasteners, mechanical fasteners, or the like. Suitable fastening systems are also disclosed in the previously incorporated PCT Patent Application WO 00/37009 published Jun. 29, 2000 by A. Fletcher et al. and the previously incorporated U.S. Pat. No. 6,645,190 issued Nov. 11, 2003 to Olson et al.

The outer cover 40 suitably comprises a material that is substantially liquid impermeable. The outer cover 40 may comprise a single layer of liquid impermeable material, or more suitably comprise a multi-layered laminate structure in which at least one of the layers is liquid impermeable. While it is not a necessity for the outer layer to be liquid permeable, it is suitable that it provides a relatively cloth-like texture to the wearer. Alternatively, the outer cover 40 may comprise a woven or non-woven fibrous web layer that has been totally or partially constructed or treated to impart the desired levels of liquid impermeability to selected regions that are adjacent or proximate the absorbent structure. The outer cover 40 may also be stretchable, and in some embodiments it may be elastomeric. Reference is made to U.S. Pat. No. 5,883,028, issued to Morman et al., U.S. Pat. No. 5,116,662 issued to Morman and U.S. Pat. No. 5,114,781 issued to Morman, all of which are hereby incorporated herein by reference, for additional information regarding suitable outer cover materials.

The bodyside liner 42 is suitably compliant, soft-feeling, and non-irritating to the wearer's skin. The bodyside liner 42 is also sufficiently liquid permeable to permit liquid body exudates to readily penetrate through its thickness to the absorbent structure 44. The bodyside liner 42 may also be stretchable, and in some embodiments it may be elastomeric. Reference is made to U.S. patent application Ser. No. 09/563,417 filed on May 3, 2000 by Roessler et al., U.S. patent application Ser. No. 09/698,512 filed on Oct. 27, 2000 by Vukos et al., both of which are incorporated by reference herein, for additional information regarding bodyside liner material.

The absorbent structure 44 is disposed between the outer cover 40 and the bodyside liner 42, which can be joined together by any suitable means such as adhesives, ultrasonic bonds, thermal bonds, or the like. While the illustrated absorbent structure 44 is shown and described herein as extending from the crotch region 26 into both the front and back waist regions 22 and 24, it is contemplated that the absorbent structure may extend from the crotch region into only the front waist region, or only the back waist region, without departing from the scope of this disclosure.

The absorbent structure 44 is suitably compressible, conformable, non-irritating to a wearer's skin, and capable of absorbing and retaining liquids and certain body wastes. For example, the absorbent structure 44 may comprise cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof.

The materials may be formed into an absorbent web structure by employing various conventional methods and techniques known in the art. For example, the absorbent structure 44 may be formed by a dry-forming technique, an air forming technique, a wet-forming technique, a foam-forming technique, or the like, as well as combinations thereof. Methods and apparatus for carrying out such techniques are well known in the art. The absorbent structure 44 may alternatively comprise a coform material such as the material disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein by reference.

Superabsorbent material is suitably present in the absorbent structure 44 in an amount of from about 0 to about 90 weight percent based on total weight of the absorbent structure. The absorbent structure 44 may suitably have a density within the range of about 0.10 to about 0.35 grams per cubic centimeter. Superabsorbent materials are well known in the art and can be selected from natural, synthetic, and modified natural polymers and materials.

In one embodiment, the absorbent structure 44 may be stretchable so as not to inhibit the stretchability of other components to which the absorbent structure may be adhered, such as the outer cover 40 and bodyside liner 42. For example, the absorbent structure may comprise materials disclosed in U.S. Pat. Nos. 5,964,743, 5,645,542, 6,231,557, 6,362,389, and international patent application WO 03/051254, the disclosure of each of which is incorporated by reference herein.

The surge management layer 45 may be attached to various components of the article 20 such as the absorbent structure 44 and/or the bodyside liner 42 by methods known in the art, such as by adhesive, ultrasonic or thermal bonding. The surge management layer 45 helps to decelerate and diffuse surges or gushes of liquid that may be rapidly introduced into the absorbent structure 44 of the article 20. Desirably, the surge management layer 45 can rapidly accept and temporarily hold the liquid prior to releasing the liquid into the storage or retention portions of the absorbent structure 44. Examples of suitable surge management layers 45 are described in U.S. Pat. No. 5,486,166; and U.S. Pat. No. 5,490,846. Other suitable surge management materials are described in U.S. Pat. No. 5,820,973. The entire disclosures of these patents are incorporated by reference herein.

Optionally, a substantially liquid permeable wrapsheet (not shown) may surround the absorbent structure 44 to help maintain the integrity of the absorbent structure 44.

The absorbent articles of the present disclosure comprise a monitoring system for detecting the presence of an insult (e.g., urine, feces, menstrual fluid, and/or blood, etc.) within the absorbent article. In general, one or more chemical sensors are used to detect the presence of a compound associated with the insult. The system monitors an electrical property of the chemical sensor (e.g., resistance and/or conductivity, etc.), and based on changes in the electrical property, determines whether the absorbent article has been insulted. After detecting the presence of the insult, a caregiver and/or a wearer of the absorbent article is signaled as to the presence of the insult. The signal may be, for example, either an auditory signal such as a song, a tactile signal such as temperature change, pressure, and/or vibration, and/or a visual signal such as a blinking light(s), a visual message, and the like. It will be understood that other signals are within the scope of the present disclosure.

Although discussed primarily in terms of detecting the presence of an insult, the monitoring system may also be used to detect the presence of water vapor in the absorbent article. As will be understood by those skilled in the art, high levels of water vapor may adversely affect the comfort level of the wearer of the absorbent article. Water vapor may be present in the absorbent article as a result of sweat or perspiration from the wearer and/or may result from certain insults such as urine. By detecting the level of water vapor in the absorbent article, a wearer and/or caregiver can monitor the comfort level of the wearer of the absorbent article.

The monitoring systems may furthermore be used to differentiate between different types of insults. As discussed herein, the absorbent articles may comprise more than one sensor. In certain embodiments, different sensors within the same absorbent article may be sensitive to compounds associated with different insults. For example, the absorbent article may comprise one sensor that is capable of detecting compounds associated with one type of insult and may further comprise a different sensor that is capable of detecting compounds associated with a different type of insult. In this instance, the caregiver and/or wearer of the absorbent article may be signalled when the presence of either or both insults are detected. In certain embodiments, the signal may be different depending on the insult, such that the caregiver and/or wearer can determine by the type of signal what type of insult has been detected.

The sensors used herein are chemiresistors. In general, a "chemiresistor" is a resistor whose electrical resistance changes upon exposure to molecules of one or more chemical species. Chemiresistors comprise a chemiresistive material disposed across or between at least one pair of spaced-apart electrodes. The chemiresistive material comprises a plurality of electrically-conductive particles suspended in a polymeric material that is sensitive to absorption or adsorption of a particular analyte (e.g., a volatile organic compound, water vapor, etc.). When the analyte absorbs or adsorbs into the polymeric material, the polymeric material swells. This swelling increases the spacing between adjacent electrically-conductive particles present in the chemiresistor, which results in an increase in electrical resistance in the chemiresistor. This change in resistance (or a corresponding change in another electrical property, such as conductance) can be measured and recorded, and used to signal a caregiver and/or a wearer of the absorbent article when an insult has occurred. Because this process is reversible (i.e., the analyte may desorb from the polymeric material, thus reducing the resistance of the chemiresistor), the chemiresistors may be used to detect multiple insults.

The chemiresistors of the present disclosure are selected to be sensitive to absorption or adsorption of certain volatile organic compounds (VOCs) and, in particular, are selected to be sensitive to VOCs that are associated with a particular body waste or exudate, such as urine, feces, menstrual fluid, and/or blood. As used herein, the term "volatile organic compound" is meant to include both the organic and inorganic metabolic gases and compounds produced by microbes present in body wastes or exudates.

Particular VOCs may be associated with one or more types of body waste. VOCs commonly associated with urine include, for example, ammonia compounds (e.g, ammonia hydroxide), short chain ($C_1$-$C_2$) acids (e.g., acetic acid), medium length ($C_8$-$C_{10}$) aldehydes (e.g., nonanal), ketones (e.g., methyl ethyl ketone), cresol (e.g., methylphenol), dimethyl disulfide, trimethylamine, limonene (e.g., 4-isopropenyl-1-methylcyclohexane), acetic acid, methyl benzoate, benzamide, benzaldehyde, and triethylamine, among others. VOCs commonly associated with feces include, for example, skatole (e.g., 3-methyl-1H-indole, 3-methylindole, etc.), mercaptans (e.g., 2-mercaptoethanol), hydrogensulfide, short chain fatty acids (e.g., myristic acid), methanethiol (e.g., 2-mercaptoethanol), and dimethylsulfide, among others. VOCs commonly associated with menstrual fluid include, for example, trimethylamine, among others.

The specificity of a chemiresistor for a particular VOC depends on the polymeric material used in the chemiresistor. In general, different polymers will absorb or adsorb VOCs with varying degrees of specificity. Suitable polymeric materials are typically selected by first determining the chemical properties of the VOC to be detected, e.g., whether the VOC is hydrophilic or hydrophobic, the polarity of the VOC, functional groups of the VOC, etc. Preferably, the chemical properties of the polymeric material selected are similar to the properties of the VOC to be detected.

In one embodiment, the polymeric material can be selected on the basis of its solubility parameter, $\delta$, which is preferably about the same as the solubility parameter of the VOC to be sorbed into the polymeric material. When the solubility parameters, $\delta$, of the polymer material and the VOC are about the same, there will be a substantial interaction between the molecules of the polymeric material and the VOC, thereby leading to a substantial sorption of the VOC into the polymeric material. Solubility parameters, $\delta$, for various polymers and VOCs can be determined from simple experiments, can be readily computed, or can be determined from tables in chemical reference books (see also U.S. Pat. No. 6,902,701, herein incorporated by reference).

The suitability of a particular polymer for detecting a VOC can also be easily and readily determined by one skilled in the art experimentally based in part on the disclosure herein. For example, once a polymer having chemical properties similar to those of the VOC to be detected has been selected, a chemiresistor comprising the polymer may then be tested (e.g., by using a method such as the one described in the examples herein) to determine if there is a resistance change when the chemiresistor is exposed to the VOC. Polymers that result in a large resistance change are preferably used in the chemiresistor.

Figure 13:
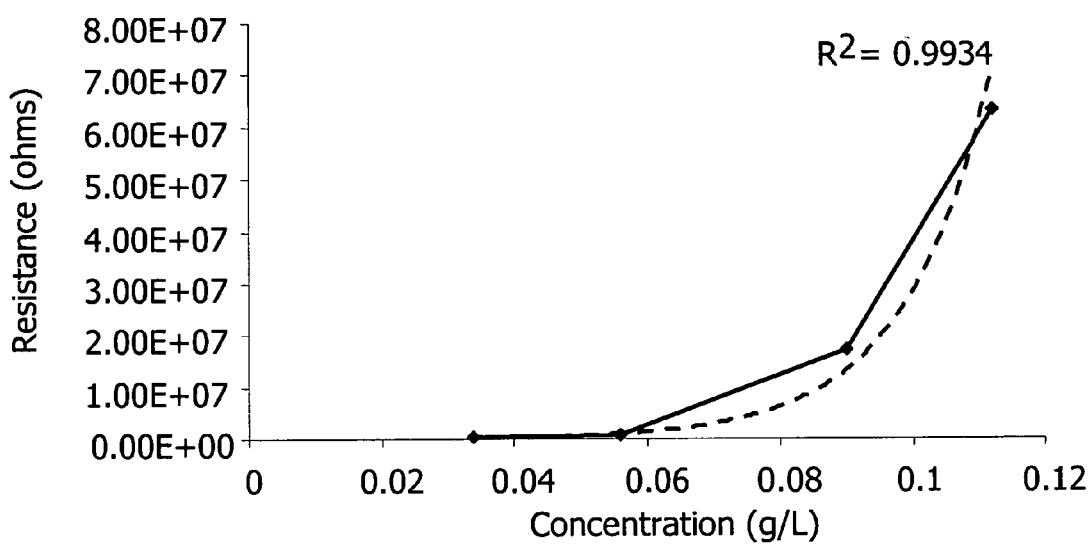
FIG. 13 illustrates the relationship between concentration (g/L) of dimethyldisulfide and the resistance (ohms) of a chemiresistor comprising poly(ethylene-vinyl acetate) (PEVA).
Figure 14:
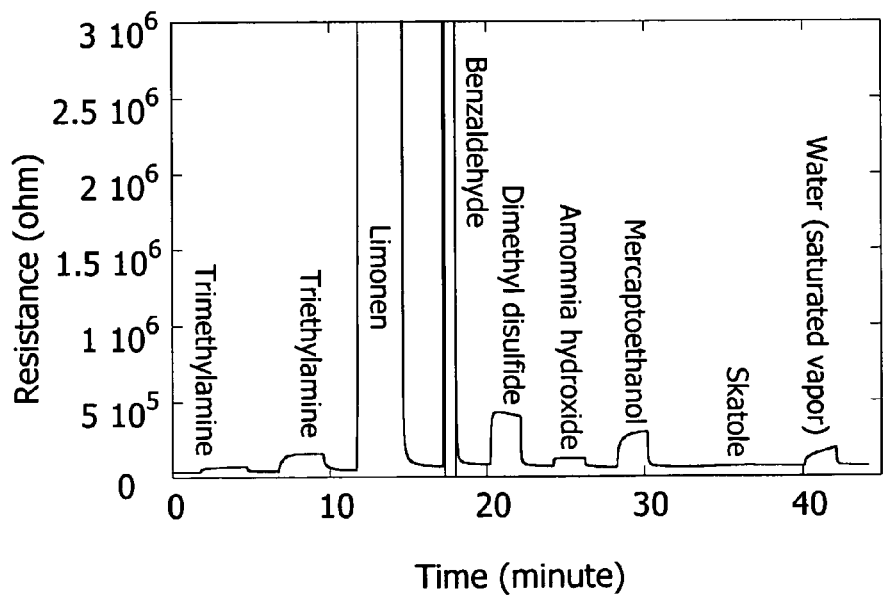
FIGS. 14 to 17 illustrate the change in resistance when chemiresistors comprising poly(ethylene-vinyl acetate) (PEVA) (FIG. 14), poly(N-vinyl pyrrolidone) (PVNP) (FIG. 15), polyisobutylene (PIB) (FIG. 16), or polyepichlorohydrin (PECH) (FIG. 17) are exposed to various compounds commonly associated with urine and/or feces, as discussed in Example 1.
Figure 15:
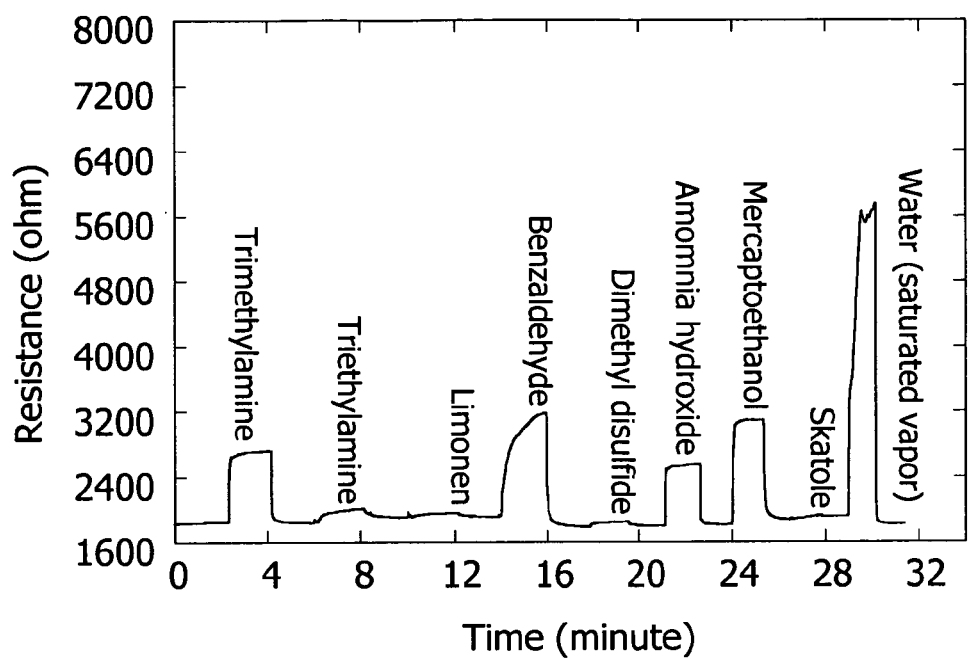
Figure 16:
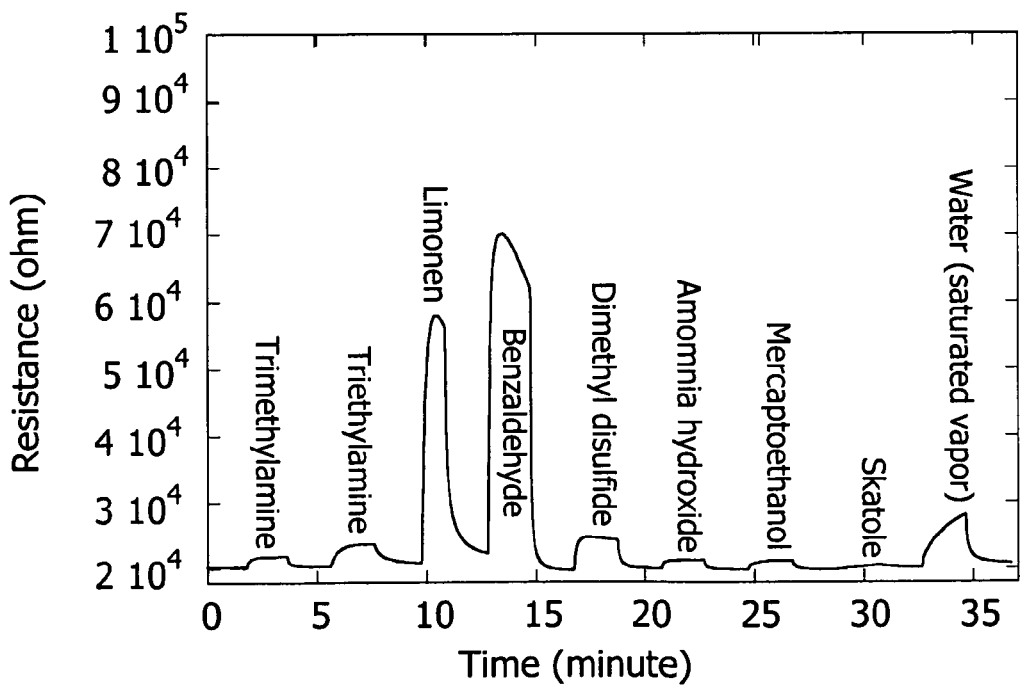
Figure 17:
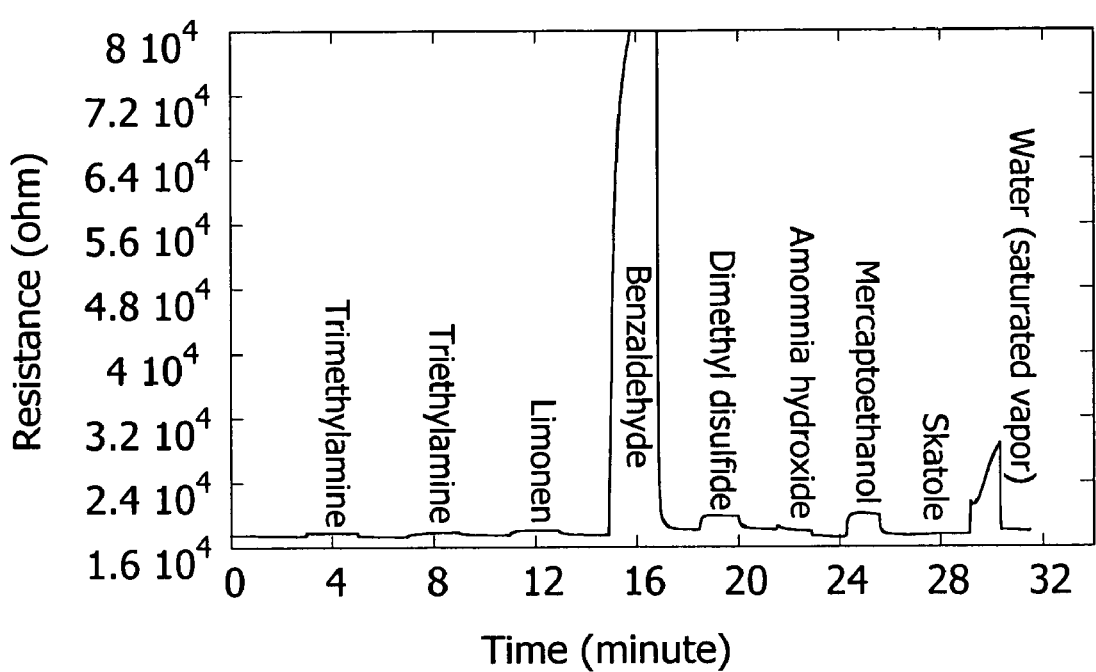

The change in resistance (or other electrical property as noted above) of the chemiresistor in the presence of a target VOC is partially dependant on the concentration of the VOC. For example, resistance of the chemiresistor will generally increase when exposed to increasing concentrations of the target VOC. An example of this is illustrated in FIG. 13, which shows the relationship between concentration of the VOC dimethyldisulfide and the resistance of a chemiresistor comprising poly(ethylene-vinyl acetate) (PEVA). It is generally preferred that a chemiresistor of the present disclosure be capable of detecting the target VOC (e.g., exhibit an increase in resistance in the presence of the target VOC or exhibit a change in another electrical property, such as conductivity) at a target VOC concentration of at least about 1 ppm.

Particular polymeric materials that can be used to form the chemiresistors used in the present disclosure include poly-epichlorohydrin (PECH), poly(N-vinyl pyrrolidone) (PVNP), polyisobutylene (PIB), poly(ethylene-vinyl acetate) (PEVA), poly(vinyl alcohol) (PVA), ethyl cellulose (EC), and poly(diphenoxyphosphazine) (PDPP), among others. Preferably, the polymeric material is selected from the group consisting of PECH, PVNP, PIB, and PEVA.

In addition to sorbing particular VOCs, certain polymers may also be sensitive to water vapor. Consequently, water vapor (e.g., from perspiration of the wearer or from the external environment) may also be sorbed by the polymeric material and affect the resistance of the chemiresistor. As discussed above with respect to VOCs, the sensitivity of a polymeric material to water vapor will depend on the chemical properties of the polymeric material. For example, chemiresistors comprising PNVP are sensitive to water vapor (i.e., have a change in resistance when exposed to saturated water vapor), while chemiresistors comprising PEVA, PIB, and PECH show little resistance change when exposed to saturated water vapor. By incorporating a chemiresistor with sensitivity to water vapor into an absorbent article, the comfort level of the wearer of the absorbent article may also be monitored.

As discussed above a polymeric material can be selected to provide a high sensitivity or selectivity for detection of a particular VOC by matching the chemical properties of the polymeric material with those of the VOC to be detected. Thus, in one embodiment, the absorbent articles of the present disclosure may comprise a single chemiresistor that is sensitive to a particular type of VOC. For example, PECH is particularly sensitive to aromatics and chlorinated hydrocarbons, as well as benzaldehydes. PVNP, a polar compound, is sensitive to polar VOCs, such as trimethylamine, benzaldehyde, ammonia, mercaptans, and water vapor. PIB and PEVA are hydrophobic and are sensitive to hydrophobic VOCs, such as limonene and benzaldehydes. PIB is also sensitive to nonpolar VOCs.

In addition, the absorbent articles of the present disclosure may comprise a single chemiresistor that is sensitive to the presence of more than one type of VOC. For example, a particular polymeric material may be sensitive to a class of VOCs that share similar functionality or chemical subgroups within their structure. A chemiresistor comprising such a polymer may show a change in resistance when exposed to any one of a number of VOCs in the class. However, the degree of change will typically be different for each individual VOC. For example, a polymer will typically be more responsive to one particular VOC than other VOCs, even if showing some change in resistance for more than one VOC in the class. Consequently, if multiple types of VOCs are to be detected, it is generally preferable to use a different chemiresistor for each individual VOC.

In another embodiment, the absorbent articles of the present disclosure may comprise more than one chemiresistor. In this embodiment, the chemiresistors may each be sensitive to different VOCs or, alternately, some or all of the chemiresistors may be sensitive to the same VOC. For example, the absorbent article may comprise multiple chemiresistors, some or all of which are sensitive to the same VOC, wherein the chemiresistors are located on different areas of the absorbent article, as discussed below. In another example, the absorbent article may comprise two or more chemiresistors, with some or all of the chemiresistors being sensitive to VOCs associated with different types of insults. In this instance, the chemiresistors may be used to differentiate between different types of insults based on the VOC detected.

In addition to the polymeric material, the chemiresistive material further comprises a plurality of electrically-conductive particles. The electrically-conductive particles provide multiple conduction pathways for an electrical current to flow when a voltage is applied between the spaced-apart electrodes. Typically the electrically-conductive particles are uniformly distributed throughout the entire volume of the chemiresistive material.

Preferably, the chemiresistive material comprises from about 20 wt. % to about 60 wt. %, and more preferably from about 30 wt. % to about 50 wt. % electrically-conductive material. In general, any electrically-conductive material may be used. Suitable electrically-conductive materials are known in the art and include, for example, carbon (e.g., graphite), metal particles such as silver, semiconductive materials, and the like. Preferably, the electrically-conductive material comprises carbon particles. The exact size of the electrically-conductive particles is not critical, but generally is from about 1 micrometer to about 10 micrometers.

The chemiresistive material can typically be prepared by dissolving the polymeric material and the electrically-conductive particles in a solvent. Typically, the solvent will have about the same solubility parameter as the polymeric material. Suitable solvents may readily be identified by one skilled in the art based on the polymeric material used. For example, water is a particularly suitable solvent for polar polymers such as PNVP. Trichloroethylene (TCE) may be used as a solvent for PECH, PEVA, and PIB. Other suitable solvents may readily be determined by one skilled in the art.

In one non-limiting example, the chemiresistive material may be prepared by dissolving the polymer material in the solvent. This may be done by mixing the polymer material and the solvent and heating the resulting mixture at approximately 40° C., or alternately, the polymer material may be allowed to dissolve in the solvent without heat. After the polymer material is dissolved, an amount of the electrically conductive particles may be added to the mixture to form a liquid chemiresistive material. In one example, the mass of electrically-conductive particles and polymer may total about 0.1 g and be mixed in about 5 ml of solvent.

As discussed above, the electrically-conductive particles are preferably uniformly distributed throughout the polymeric material. In one embodiment, a surfactant such as a non-ionic surfactant can optionally be added to the liquid chemiresistive material mixture to help prevent aggregation or agglomeration of the electrically-conducting particles or migration of these particles towards the electrodes when a voltage is applied to the chemiresistor. Furthermore, the liquid chemiresistive material may optionally be sonicated to disperse the electrically-conductive particles throughout the polymeric material, and to help prevent the formation of agglomerated colloids. In addition, the liquid chemiresistive material may optionally be filtered to remove any agglomerated colloids formed by the electrically-conductive particles. Filtration may be done using, for example, a filter with a pore size of about 5 μm.

The liquid chemiresistive material is then deposed on the absorbent article across or between a pair of spaced-apart electrodes. By "spaced-apart" it is meant that the electrodes are not directly touching each other. Although the chemiresistive material is generally deposed across the electrodes, it will be recognized that the chemiresistive material may also be deposed between the electrodes. In this instance, the chemiresistive material should be close enough to each electrode so that the chemiresistive material is in electrical connection with the electrodes (e.g., forms a circuit, as discussed below). Thus, as used herein, the phrase "disposed across a pair of spaced-apart electrodes" is intended to include instances where the chemiresistive material is disposed across and/or between the electrodes such that the chemiresistive material is in electrical connection with the electrodes.

The electrodes may be constructed of any material that is generally electrically conductive. For example, the electrodes may be constructed of metal strips (e.g., aluminum strips), metal films, metal wire, foil, coated films, conductive polymers, conductive inks, or conductive threads, among others. Other electrodes are within the scope of this disclosure. The electrodes may be attached to the absorbent article by any suitable means including, for example, by using adhesives, printing the electrodes onto the a suitable surface of the absorbent article, and the like. The liquid chemiresistive material may be deposited across the electrodes by any suitable means, including, for example, spin coating, spray coating, inkjet deposition, printing, etc. Preferably, the chemiresistive material is deposed across the electrodes by printing.

The chemiresistor may be located on any suitable surface of the absorbent article. Preferably, the chemiresistive material is deposited onto a non-porous surface of the absorbent article such as, for example, the outer cover. In one embodiment, the chemiresistive material is deposited on the absorbent-facing surface of the outer cover to form a chemiresistor. Since the outer cover may be composed of a "breathable" material which permits vapors to escape from the absorbent body while still preventing liquid exudates from passing through the outer cover, VOCs from an insult in the absorbent article may still reach the chemiresistor by passing through the outer cover. Thus, the chemiresistive material may alternatively or additionally be deposited on the outer surface of the outer cover to form a chemiresistor.

Optionally, when the chemiresistor is located on the outer surface of the outer cover of the absorbent article, the chemiresistor may be covered with a coating comprising, for example, a non-porous, non-breathable substrate, such as a film or printed or layered material. Such a coating helps to isolate the chemiresistive material from the external environment and reduce the likelihood of the polymeric material sorbing any VOCs or water vapor from the external environment.

The specific location of the chemiresistor in the absorbent article is not limited and will vary depending on the VOC and the body waste to be detected and on the type of absorbent article. For example, in one preferred embodiment, a chemiresistor may be located in the crotch region of the absorbent article, as illustrated in FIGS. 2-4. Alternately, or in addition, a chemiresistor may be located in other regions of the absorbent article.

One or more of the chemireisistors described herein form a part of the wetness monitoring system. In general, the monitoring system comprises a circuit. The chemiresistive material is disposed across a pair of spaced apart electrodes that are electrically connected to a current source. A measuring device measures an electrical property of the circuit, e.g., resistance, conductance, voltage, etc., and sends a signal containing information on the electrical property to a microprocessor. The microprocessor analyzes the signal to determine if an insult has occurred. If the microprocessor determines that an insult has occurred, an indicator means (also referred to herein as an insult alarm) is activated to signal a caregiver and/or a wearer of the absorbent article of the presence of the insult. Alternately, the microprocessor, upon determining that an insult has occurred, may activate a transmitter, which may then send a signal that an insult has occurred to a receiver at a remote location. The receiver then activates an indicator means to signal a caregiver or a wearer of the absorbent article of the presence of the insult.

As will be apparent from the discussion herein, the components of the monitoring system (e.g., measuring device, microprocessor, analog-to-digital converter, indicator means, and/or transmitter, etc.) may be housed together or separately, and attached to the absorbent article. Alternately, certain components of the monitoring system may be present at a remote location. For example, in one embodiment, the measuring device, microprocessor, analog-to-digital converter, and/or transmitter are housed together or separately and attached to the absorbent article, while the receiver and/or indicator means are housed together or separately at a remote location. As used herein, "remote location" means the components are not attached to the absorbent article. For example, in one embodiment, the receiver and/or indicator means may be housed in a transportable unit that may be kept with the caregiver. Examples of such a unit may include an alarm such as a bed side alarm, alarm clock, beeper, or pager, a lamp, a wall clock, and the like.

In one particularly suitable embodiment, shown best in FIGS. 2-4, one example of the wetness monitoring system is generally indicated by reference numeral 70. The monitoring system 70 includes a chemiresistor 72 for detecting the presence of a VOC associated with an insult, as discussed above. The chemiresistor 72 is deposed in the crotch region 26 across a pair of spaced apart electrodes E1, E2. The electrodes E1, E2 extend from the chemiresistor 72 in the crotch region 26 to the front waist region 22 of the pants 20. As shown best in FIG. 5, the electrodes E1, E2 may be disposed on the outer surface of the outer cover, although the electrodes (and chemiresistors) may be disposed at other locations, as discussed above, without departing from the scope of this disclosure.

Figure 6:
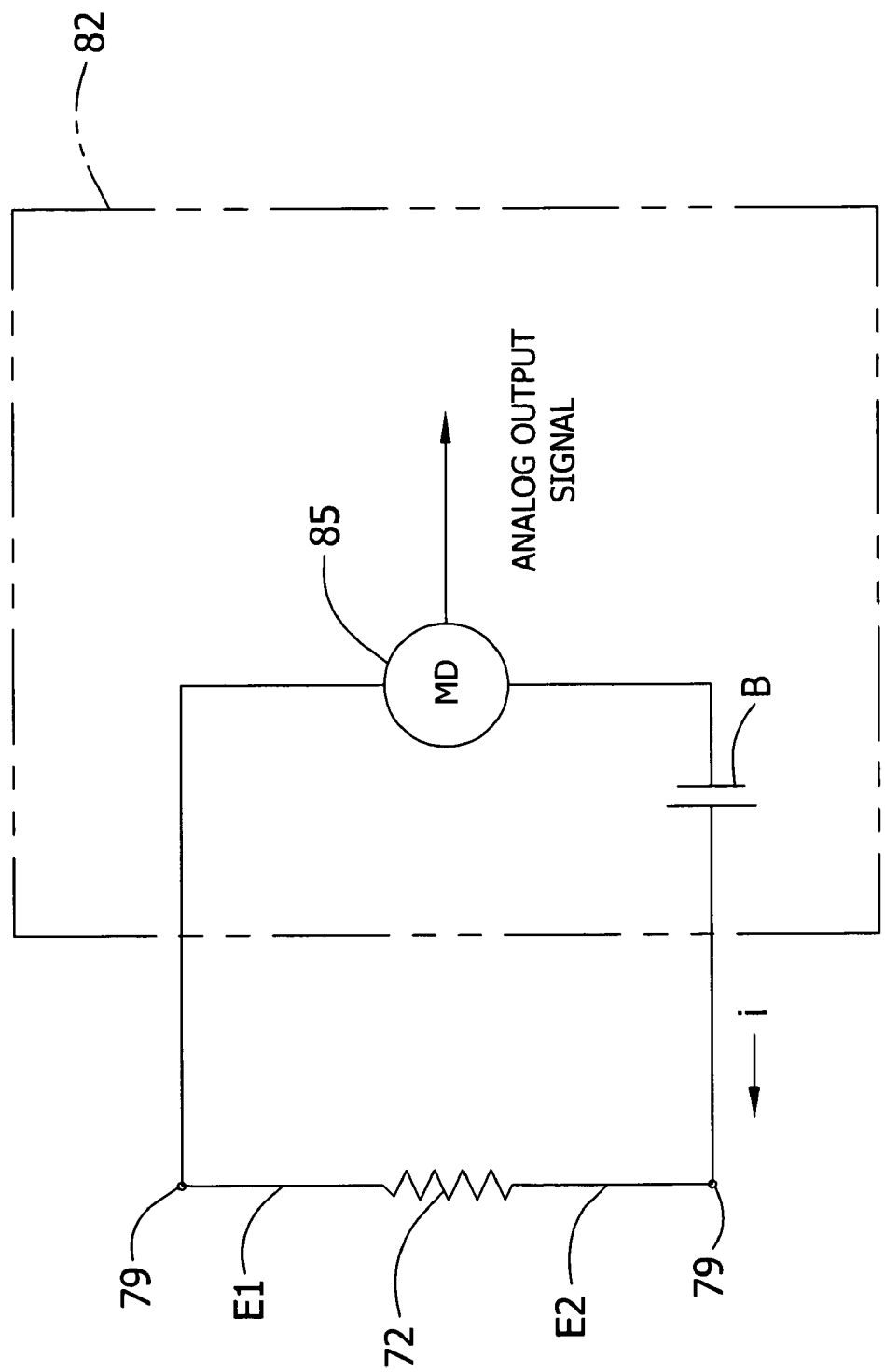
FIG. 6 is a schematic illustration of the pants and one embodiment of a monitoring system of the present disclosure.

Current i from a current source B (illustrated schematically in FIG. 6) runs through the electrodes E1, E2. The current source i may be a direct current source such as a battery (as illustrated), or an alternating current source. In the illustrated embodiment, the electrodes E1, E2 are electrically connected to the current source by way of electrically conductive snap fasteners 79. However, any suitable means of electrically connecting the electrodes to the current source are within the scope of this disclosure such as, for example, a clamp connector, conductive hook and loop fasteners, conductive adhesives (e.g., conductive tape), and the like. As illustrated in FIG. 3, each corresponding end of each electrode E1, E2 is connected to a first snap fastener member 79A located in the front waist region 22 of the pants 20. Alternatively, the first snap fastener member (or other connection means) may be located in the back waist region 24, or on other suitable locations on the pants 20. A housing unit 82 that houses the current source i has corresponding second snap fastener elements 79B for engaging the first snap fasteners 79A and securing the housing to the pants 20. In addition to the current source i, the housing unit 82 of the present embodiment may also house the remaining components of the wetness monitoring system 70 that will be described hereinafter, although, as discussed above, it is contemplated that the housing unit may include only some or none of the remaining components. In the illustrated embodiment the housing unit 82 is releasably secured to the pants 20 by way of the snap fasteners 79, although it is understood that the housing unit may be releasably secured to the absorbent article by other means, such as clamps, conductive hook and loop fasteners, conductive adhesives (e.g., conductive tape), and the like, or alternatively, may be permanently secured to the absorbent article by any suitable means, without departing from the scope of this disclosure. In one embodiment, when the housing unit is releasable secured to the absorbent article, the housing unit may be reused, for example, by attaching the housing unit to a new absorbent article when the old absorbent article is changed.

In certain embodiments, the absorbent article may comprise two or more chemiresistors. In this instance, the chemiresistive material of the first chemiresistor may be deposed across a first pair of spaced apart electrodes and the chemiresistive material of at least one additional chemiresistor may be deposed across at least one different pair of spaced apart electrodes. Each pair of spaced apart electrodes may then be connected to the current source, as discussed above.

A measuring device 85 (FIG. 6) measures an electrical property of the circuit. In one embodiment, the resistance R of the chemiresistor 72 is measured. Because the electrodes E1, E2 are spaced apart, current from the current source i must pass through the chemiresistor 72 to complete a circuit. As discussed above, when a VOC absorbs or adsorbs into the polymeric material of the chemiresistor, the polymeric material swells. This swelling increases the spacing between the electrically-conductive particles present in the chemiresistor, which results in an increase in electrical resistance in the chemiresistor. This change in resistance can be monitored and used to determine if an insult is present in the absorbent article. Although discussed primarily in terms of resistance, other electrical properties of the circuit, including voltage, conductivity, and impedance, among others, may also change based on a change in the resistance of the chemiresistor. As such, these electrical properties may also be measured and used to determine if an insult is present in the absorbent article, without departing from the scope of this disclosure.

The measuring device 85 produces an analog output signal (FIG. 6) indicative of the electrical property of the circuit that is being measured. For example, the measuring device 85 can measure a voltage drop across the chemiresistor 72, and produce an analog output signal corresponding to the voltage drop. The output voltage signal can be used to determine other electrical properties, such as resistance or conductivity, by performing suitable calculations known in the art or using a reference table. For example, as is well known in the art, the voltage drop is indicative of the resistance of the chemiresistor when the current is constant. Thus, as explained below in further detail, the resistance of the chemiresistor 72 may be determined using the analog output signal of the measuring device 85.

Figure 7:
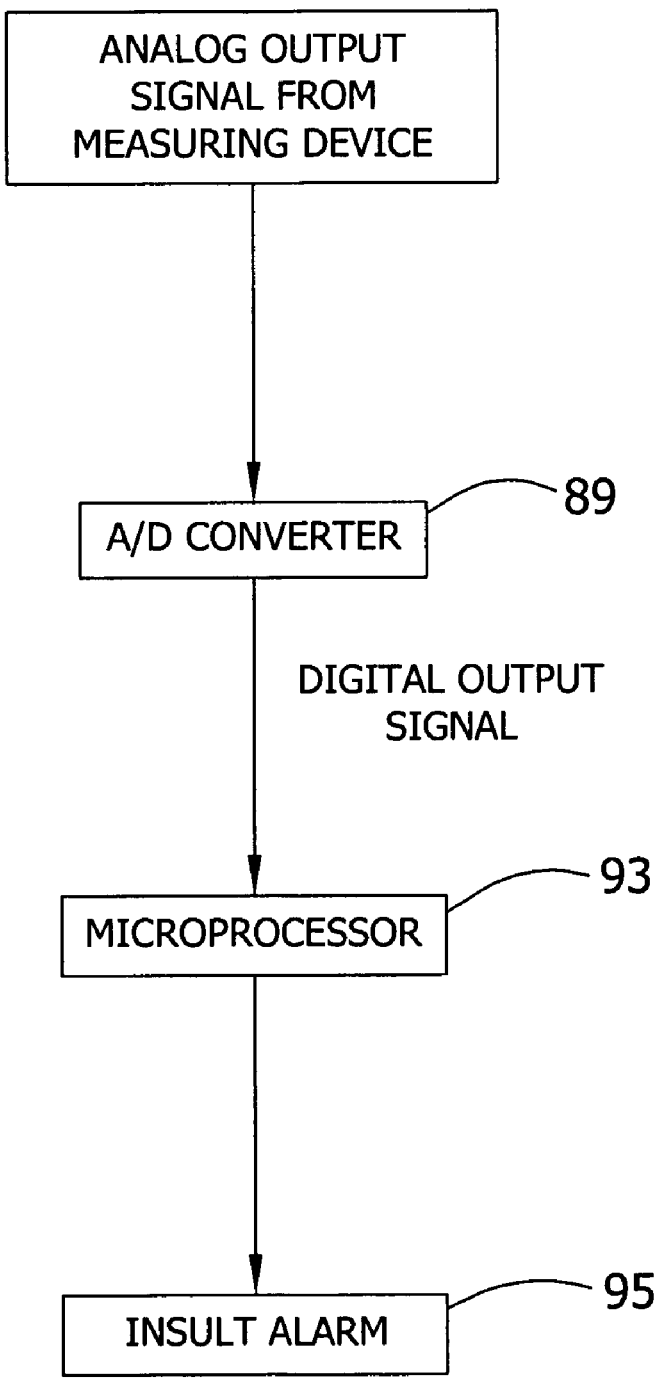
FIG. 7 is a block diagram for one embodiment of the disclosure illustrating an order of operation for components/devices of the disclosure, including a measuring device for measuring an electrical property of the pants and an analog-to-digital converter for converting an analog output from a measuring device into digital values to be read by a microprocessor.

In one embodiment, illustrated in FIG. 7, an analog-to-digital converter 89 receives the analog output signal from the measuring device 85 and converts the signal into a digital output signal. A microprocessor 93 receives the digital output signal, which is representative of the magnitude of the electrical property (e.g., voltage, resistance, conductivity, etc.), and analyzes it to determine the presence of an insult. If the microprocessor 93 detects the presence of an insult, then it activates the insult alarm 95. Alternately, the microprocessor activates a transmitter (not shown) that sends a signal to a receiver at a remote location, and the receiver (which may be a separate device or a component of the insult alarm) activates an insult alarm. The insult alarm (i.e., indicator means) then signals a caregiver and/or a wearer of the absorbent article of the presence of an insult. As discussed above, the signal may be auditory, visual, and/or tactile, among others.

The analog-to-digital converter 89 is a conventional device for converting analog signals into digital signal that can be read by a microprocessor. The analog-to-digital converter 89 of the present embodiment may be a separate device or it may be a component of the microprocessor 93. For illustrative purposes, the electrical property will hereinafter be referred to as resistance although, as noted above, it may be any of a number of suitable properties.

Figure 12:
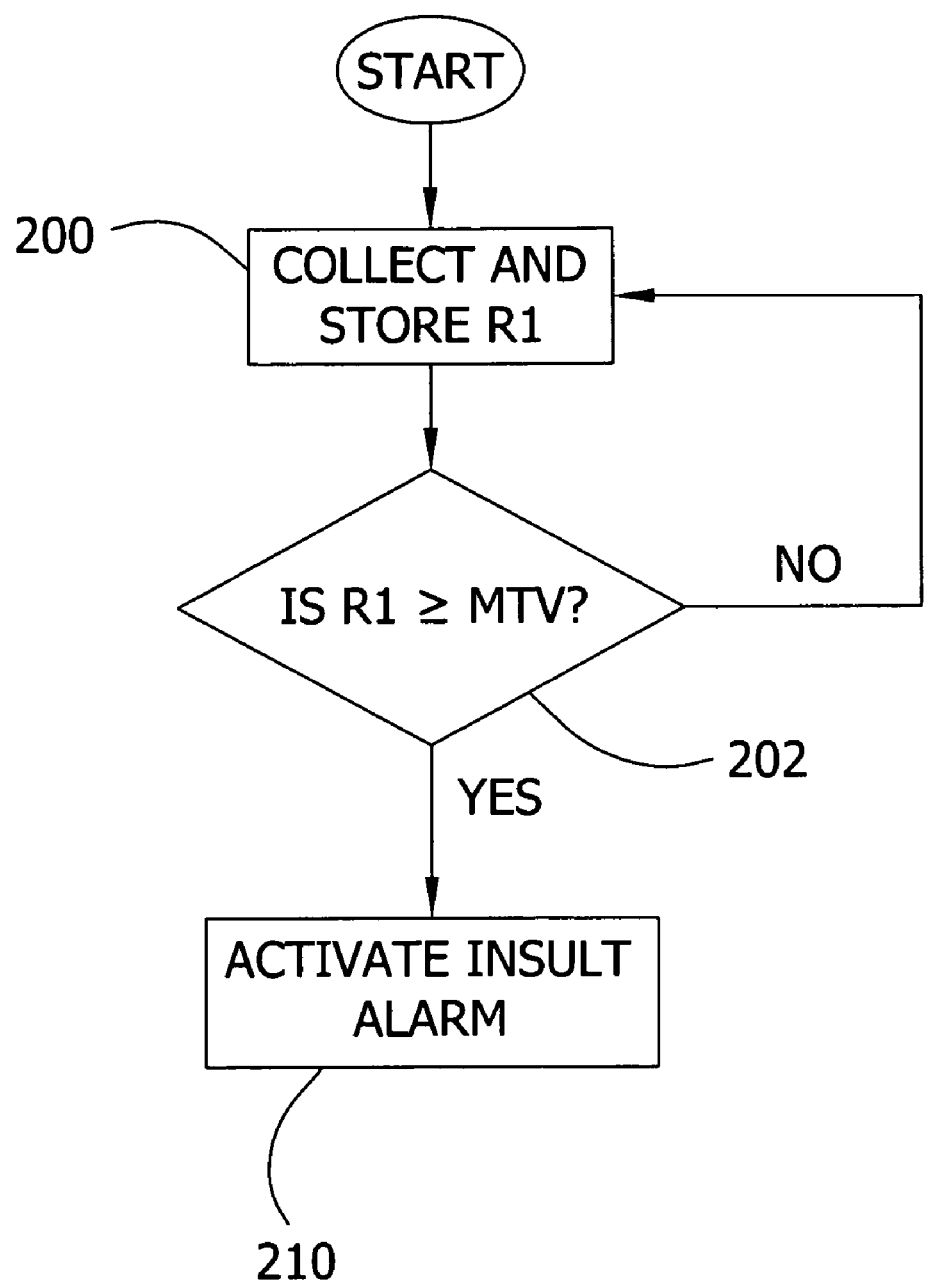
FIG. 12 is block diagram of another embodiment of the present disclosure illustrating instructions for the microprocessor for determining whether an insult has occurred.

In one embodiment, the analog output signal from the measuring device 85 is converted into a digital output signal and sent to the microprocessor 93, as illustrated in FIG. 7 and explained above. Although this and other illustrated embodiments described herein use an all digital approach, it is understood that other examples may also use in part or in whole an analog approach, as would be generally understood by those in the art. Referring to FIG. 12, the microprocessor 93, at instruction 200, collects and stores resistance value (R1) (or other electrical property) from the digital output signal. At instruction 202 the microprocessor 93 compares the measured resistance value (R1) (broadly, the magnitude indicator value) to a magnitude threshold value (MTV) to determine whether the measured resistance is an indication of the presence of an insult (broadly, a first test).

If the comparison is not indicative of the presence of an insult (i.e., the measured resistance value, R1, is less than the magnitude threshold value), then the microprocessor 93 is instructed to repeat the above steps and continue collecting, storing and comparing subsequent resistance values until the comparison of such to the magnitude threshold value is indicative of the presence of an insult (i.e., the measured resistance value, R1, is greater than or equal to the magnitude threshold value, MTV). If the comparison is indicative of the presence of an insult, then the microprocessor 93 activates the insult alarm at instruction 210. Alternately, the microprocessor activates a transmitter (not shown) that sends a signal to a receiver at a remote location, and the receiver activates the insult alarm, as discussed above.

Typically, the magnitude threshold value will correspond to the resistance of the chemiresistor in the presence of the targeted VOC. As discussed above, a chemiresistor will have varying degrees of sensitivity to different VOCs depending on the polymeric material used in the chemiresistor and the VOC to be detected. As such, the magnitude threshold value will vary depending on both the chemiresistor used and the VOC to be detected. Magnitude threshold values for different combinations of chemiresistor and VOC may be determined experimentally, for example, by determining the resistance of the chemiresistor in the presence of the VOC to be detected (e.g., by using methods such as those described in the examples herein).

For example, a magnitude threshold value may be determined by determining the baseline resistance level for a chemiresistor in the absence of any VOCs, and the resistance level of the chemiresistor in the presence of a target VOC. The magnitude threshold value for that particular chemiresistor/VOC combination may then be set at any resistance level in between these two values. The particular choice of magnitude threshold values will vary depending on the desired sensitivity of the chemiresistor. Typically, a higher magnitude threshold value is chosen if it is desired to avoid false positive determinations of the presence of an insult, and a lower threshold value is chosen if greater sensitivity of the chemiresistor is desired. In one non-limiting example, if the baseline resistance of a chemiresistor is measured at 10 kilo ohms and the resistance of the same chemiresistor is 3 mega ohms in the presence of a target VOC, then a magnitude threshold value of 1 mega ohm may be suitable for that particular chemiresistor/VOC combination to substantially avoid false positive readings.

In one embodiment of the present disclosure, a percent difference test is conducted on the measured resistance of the chemiresistor 72 to determine the presence (or lack thereof) of an insult in the absorbent article as the absorbent article is being worn by the wearer. In this embodiment, a proportional difference (e.g., a percent difference) in the measured electrical property of the chemiresistor over time is determined, and this proportional difference is compared with a difference threshold value to determine if an insult is present in the pants.

Figure 8:
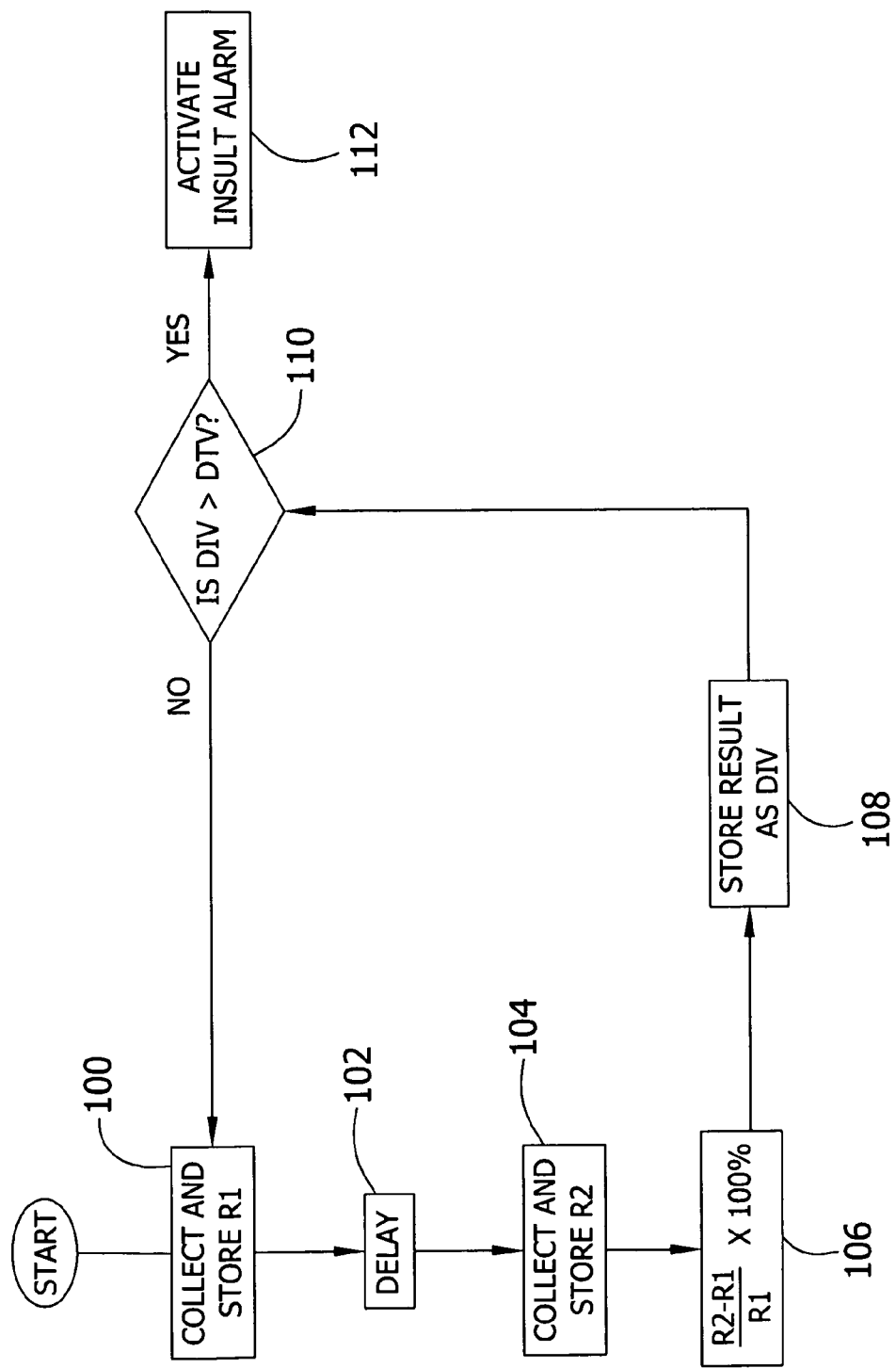
FIG. 8 is a block diagram of exemplary instructions for the microprocessor of the present disclosure for determining the presence of an insult using a proportional difference of the measured resistance of the pants.

FIG. 8 illustrates schematically the instructions of the microprocessor 93 for determining the percent difference in the resistance of the chemiresistor 72 and comparing the percent difference to a difference threshold value to determine the presence of an insult. At instruction 100 the microprocessor 93 collects and stores in its memory a first resistance value (R1) from the digital output signal. The microprocessor 93 then delays sampling for a period of time at instruction 102 before collecting and storing a second resistance value (R2) at instruction 104. The delay may be programmed or may be a function of the sampling rate of the A/D converter 89 and/or the microprocessor 93.

With the stored first and second resistance values (R1, R2), at instruction 106 the microprocessor 93 subtracts the first value (R1) from the second value (R2) and divides the resulting difference by the first value (R1) and multiplies the resulting quotient by 100%. The resulting value is stored as a difference indicator value (DIV) at instruction 108.

At instruction 110, the resulting difference indicator value (DIV) is then compared to a difference threshold value (DTV) to determine if an insult is present. For example, if the difference indicator value (DIV) is greater than the difference threshold value (DTV) then this is indicative of the presence of an insult. As an example, the difference threshold value (DTV) may be a value between 10% and 20% (indicating a 10% and 20% increase in resistance due to the target VOC sorbing into the chemiresistor), or more particularly, the difference threshold value may be about 15%. If the comparison of the difference indicator value to the difference threshold value is indicative of the presence of an insult, then, if there are no other indicators, the microprocessor 93 activates the insult alarm 95 at instruction 112 to inform the caregiver and/or the wearer of the presence of an insult. If, however, the comparison of the difference indicator value (DIV) to the difference threshold value (DTV) is not indicative of the presence of an insult, then, if there are no other indicators, the microprocessor 93 is instructed to repeat the above steps for determining new difference indicator values and comparing them to the difference threshold value until an insult is indicated.

The percent difference test is meant to be more accurate (that is, detects insults better and detects false-positives less frequently) than the conventional magnitude threshold test because the percent difference test is independent of the magnitude of the resistance of the chemiresistor prior to absorption or adsorption of a VOC. The percent difference test focuses on the amount of change in the resistance and allows for more accurate detection of multiple voids.

In another example of the difference embodiment, the instructions for the microprocessor 93 may involve determining the percent difference between previous successive resistance values compared to a present value, e.g., the difference between a third resistance value (R3) and second resistance value (R2) and the third value (R3) and a first resistance value (R1).

Figure 9:
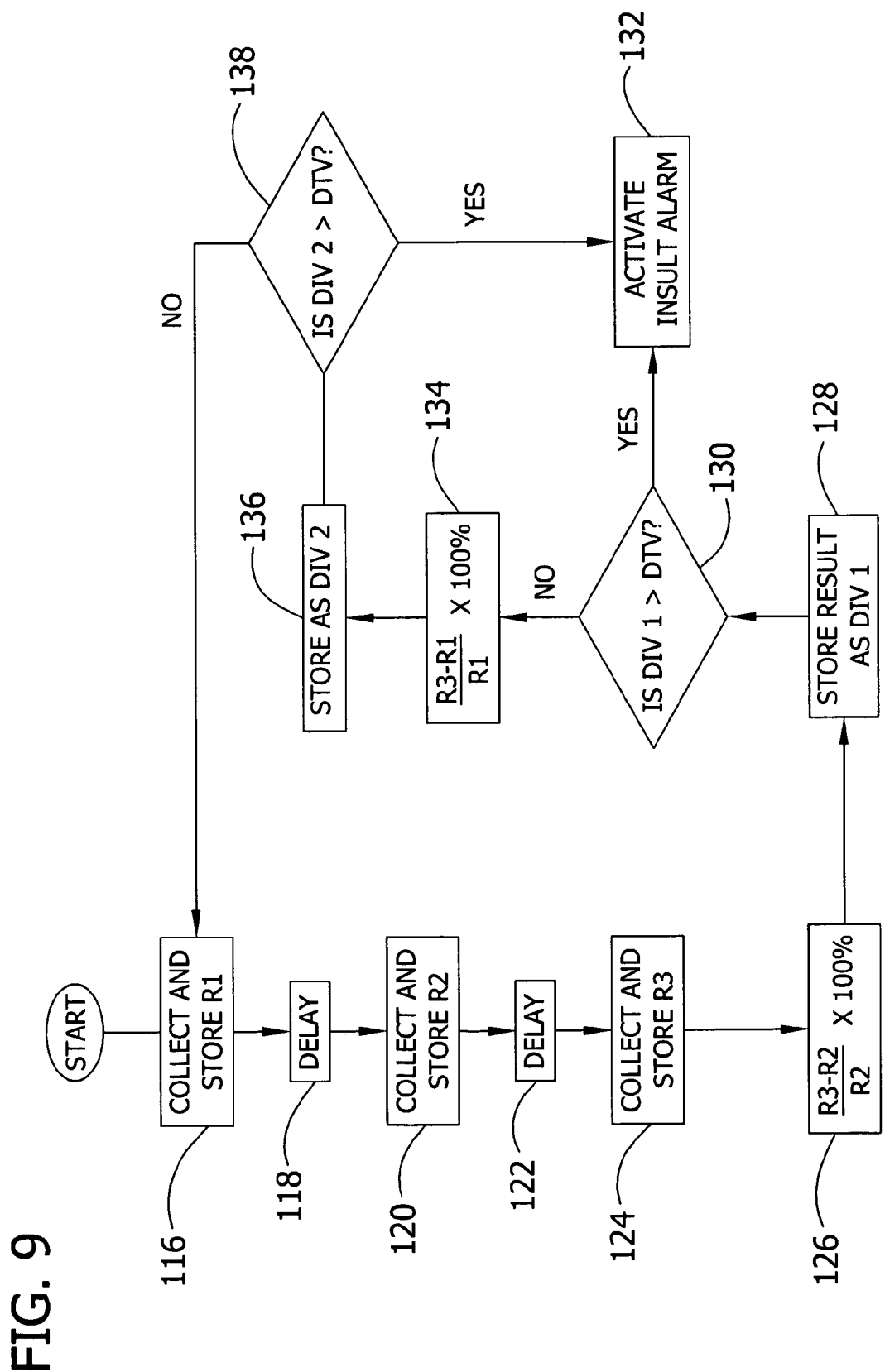
FIG. 9 is a block diagram of exemplary instructions for the microprocessor of the present disclosure for determining the proportional difference of the measured resistance of the pants using successive resistance values.

FIG. 9 illustrates schematically the instructions of the microprocessor for this embodiment. At instruction 116 the microprocessor 93 collects and stores in its memory a first resistance value (R1) from the digital output signal at a first time. The microprocessor then delays for a period of time at instruction 118 before collecting and storing a second resistance value (R2) at instruction 120. At instruction 122 the microprocessor 93 delays, and then it collects and stores a third resistance value (R3) at instruction 124. With the values stored, the microprocessor 93 subtracts the second value (R2) from the third value (R3) and divides the resulting difference by the second value (R2) at instruction 126 to get a percent difference. The percent difference is stored as a first difference indicator value (DIV 1) at instruction 128 and compared to the difference threshold value (DTV) at instruction 130 to determine if the comparison is indicative of the presence of an insult.

If the comparison of the first difference indicator value (DIV 1) is indicative of the presence of an insult, then the insult alarm 95 is activated at instruction 132. If the comparison is not indicative of the presence of an insult then the microprocessor is instructed at 134 to calculate a second difference indicator value (DIV 2) by subtracting the first value (R1) from the third value (R3) and dividing the difference by the first value (R1). This second percent difference (DIV 2) is stored as the second difference indicator value (DIV 2) at instruction 136. At instruction 138 the second difference indicator value (DIV 2) is then compared to the difference threshold value (DTV).

If the comparison of the second difference indicator value (DIV 2) to the difference threshold value (DTV) is indicative of the presence of an insult, then the insult alarm is activated at the instruction 132. If the comparison is not indicative of the presence of an insult, then the microprocessor is instructed to repeat the above steps for comparing a new difference indicator value to the difference threshold value until an insult is indicated.

In the above example, if either the first indicator value (DIV 1) or the second indicator value (DIV 2) is above the difference threshold value (DIV), the microprocessor 93 activates the insult alarm 95. It is also contemplated that only when both the first indicator value and the second indicator value are greater than the threshold value (i.e., both comparisons are indicative of the present of an insult) would the alarm 95 be indicated.

In another embodiment of the present disclosure, a rate of change test is conducted on the measured electrical property of the circuit to determine the presence (or lack thereof) of an insult. In this embodiment, a rate of change of the measured electrical property over a period of time is determined, and this rate of change is compared with a rate threshold value to determine if an insult is present in the absorbent article.

Figure 10:
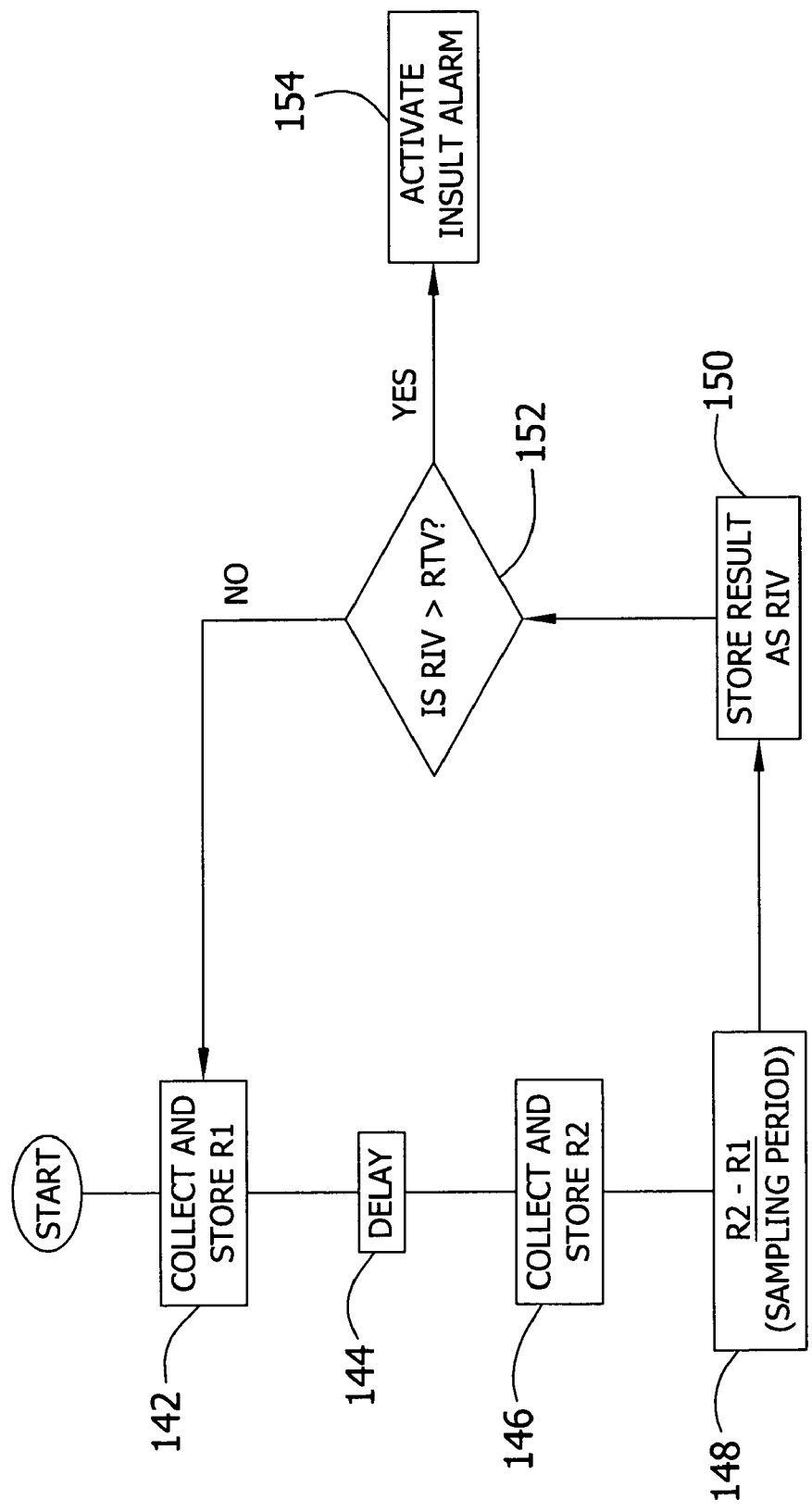
FIG. 10 is a block diagram of exemplary instructions for the microprocessor of the present disclosure for determining the presence of an insult using a rate of change of the measured resistance of the pants.

In one example of this embodiment, the output signal from the measuring device is converted to a digital output signal (via the analog-to-digital converter 89, for example) and received by the microprocessor 93 as explained above and shown in FIG. 7. FIG. 10 illustrates schematically one example of the instructions of the microprocessor 93 for determining the rate of change in, for example, the resistance of the chemiresistor 72 and comparing the rate of change to a rate threshold value to determine the presence of an insult. At instruction 142 the microprocessor 93 collects and stores in its memory a first resistance value (R1) from the digital output signal at a first time. The microprocessor 93 then delays for a period of time at instruction 144 before collecting and storing a second resistance value (R2) at instruction 146. As explained above, the delay is determined by the sampling period of the A/D converter 89 and/or is programmable by instructions within the microprocessor 93.

With the stored first and second values (R1, R2), the microprocessor 93 subtracts the first value from the second value and divides the resulting difference by the sampling period at instruction 148. The resulting value is stored as a rate indicator value (RIV) at instruction 150. At instruction 152, the microprocessor 93 compares the resulting rate indicator value (RIV) to a rate threshold value (RTV) to determine if an insult is present. For example, if the rate indicator value (RIV) is greater than the rate threshold value (RTV) then this is indicative of the presence of an insult. If the comparison of the rate indicator value to the rate threshold value is indicative of the presence of an insult, then, if there are no other indicators, the microprocessor 93 activates the insult alarm 95 to inform the caregiver and/or the wearer of the presence of an insult at instruction 154. If, however, the comparison of the rate indicator value to the rate threshold value is not indicative of the presence of an insult, then, if there are no other indicators, the microprocessor 93 is instructed to repeat the above steps for determining new rate indicator values and comparing them to the rate threshold value until an insult is indicated.

A suitable rate threshold value for a particular chemiresistor/VOC combination may vary depending on the desired sensitivity of the chemiresistor. For example, a rate threshold value for a particular chemiresistor/VOC combination may be determined by measuring the resistance level of the chemiresistor in the absence of any VOCs (R1), exposing the chemiresistor to the target VOC, and measuring the peak resistance level of the chemiresistor in the presence of the target VOC(R2). The R1 value may then be subtracted from the R2 value, and the resulting difference divided by the time it took for the chemiresistor to reach its peak resistance level after exposure to the target VOC (alternately, the change in resistance could be measured for a predetermined amount of time, for example, the change in resistance over 3 seconds could be used to calculate the rate of resistance change). This value (ohms/second) is an observed rate of increase in resistance of the chemiresistor in the presence of the target VOC. Any value below this observed rate of increase may be selected as the rate threshold value. Typically, a higher rate threshold value is chosen if it is desired to avoid false positive determinations of the presence of an insult, and a lower rate threshold value is chosen if greater sensitivity of the chemiresistor is desired. In one non-limiting example, if the observed rate of increase in resistance for a particular chemiresistor/VOC combination is 100 kilo ohms/sec., the rate threshold value will be some value below the observed rate of increase, such as, for example, 80 kilo ohms/sec.

Like the percent difference test discussed above, the rate of change test is meant to be more accurate (that is, detects insults better and detects false-positives less frequently) than the conventional magnitude threshold test because the rate of change test is independent of the magnitude of the resistance of the chemiresistor prior to absorption or adsorption of a VOC and focuses on how quickly the property changes.

Figure 11:
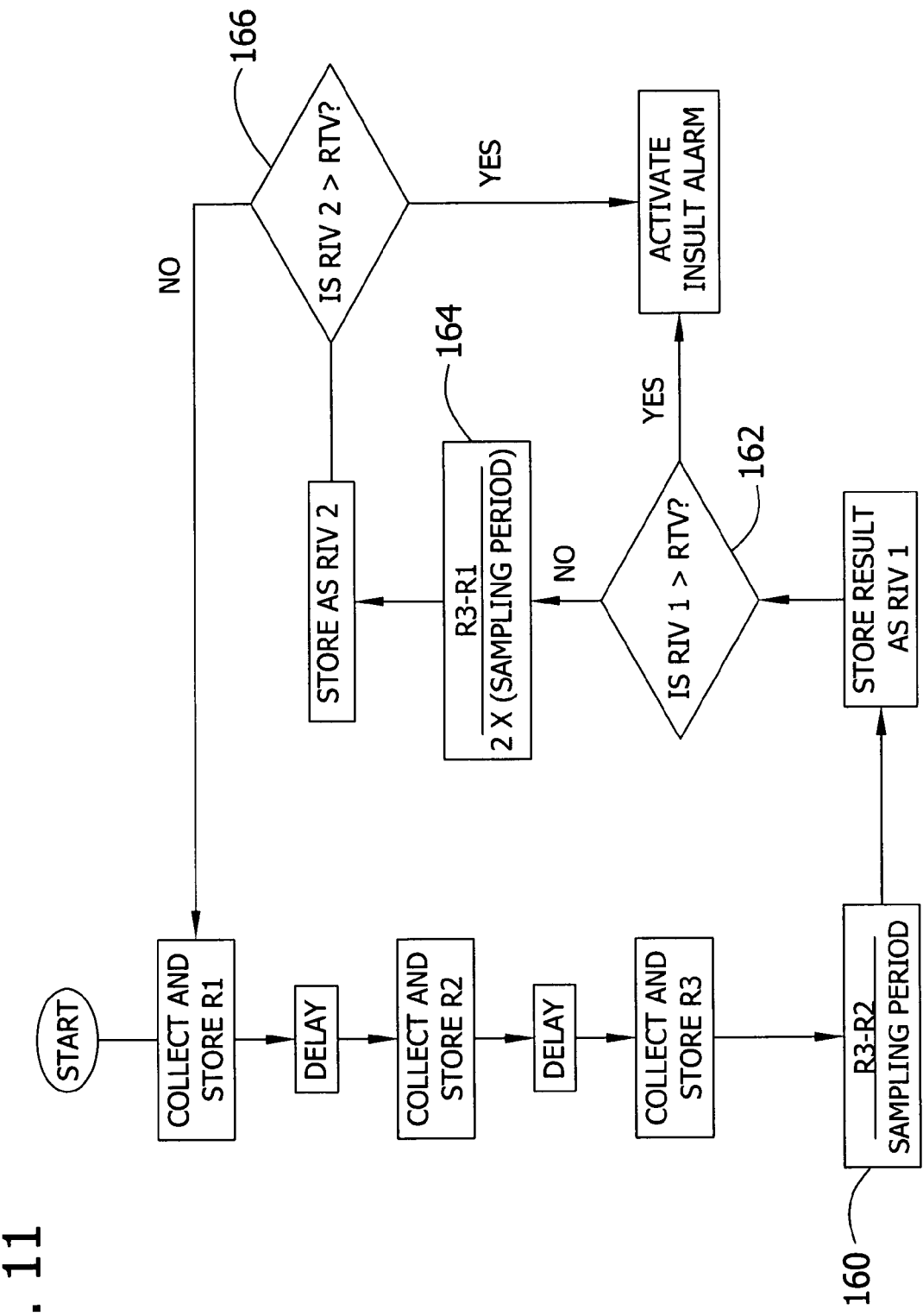
FIG. 11 is a block diagram of exemplary instructions for the microprocessor of the present disclosure for determining the rate of change of the measured resistance of the pants using successive resistance values.

As illustrated in FIG. 11, in another example of the rate of change embodiment, the instructions for the microprocessor may involve determining the rate of change between previous successive values compared to a present value (e.g., the rate of change between a third value and second value and a third value and first value). This example is substantially similar to the instruction given in FIG. 9 with respect to the percent difference embodiment, except that the first rate indicator value (RIV 1) between third value (R3) and the second value (R2) is determined at instruction 160 and compared to the rate threshold value (RTV) at instruction 162, and the second rate indicator value (RIV 2) between third value (R3) and the first value (R1) is determined at instruction 164 and compared to the rate threshold value (RTV) at instruction 166.

In another embodiment, both the percent difference embodiment and the rate of change embodiment may be combined into a single embodiment, whereby the insult alarm 95 is activated only if both the comparison of the difference indicator value (DIV) to the difference threshold value (DTV) and the comparison of the rate indicator value (RIV) to the rate threshold value (RTV) are indicative of the presence of an insult. Alternatively, the insult alarm may be activated if either the comparison of the difference indicator value to the difference threshold value or the comparison of the rate indicator value to the rate threshold value are indicative of the presence of an insult.

One example of this embodiment (not shown) is a combination of the examples of FIGS. 8 and 10 (using R2-R1) or FIGS. 9 and 11 (using R3-R2 and R3-R1) where the analog output signal from the measuring device is converted to a digital output signal and the microprocessor is instructed to compute both the rate indicator values and the difference indicator values and compare both values to respective threshold values to determine the presence of an insult using the digital output signal.

As previously discussed, certain polymeric materials are sensitive to water vapor, in addition to certain VOCs. Consequently, water vapor from perspiration of the wearer or from the external environment may be sorbed into the polymeric material and affect the resistance of the chemiresistor. Therefore, in one embodiment, this water vapor is accounted for by determining the resistance of the chemiresistor in the presence of a baseline water vapor level. For example, the resistance of the chemiresistor may be measured over a period of time and used to calculate an average resistance value. This average resistance value accounts for water vapor that may have sorbed into the chemiresistor in the absence of an insult. This average may then be used, for example, as the R1 value in the rate of change or percent difference test.

As will be apparent to those skilled in the art, numerous variations of the above described tests as well as other conventionally known tests may be performed by the microprocessor to determine if an insult is present in the absorbent article.

It is understood that the exemplary values and range of values, given for the above tests/checks, including exemplary values given for the difference threshold value (DTV), the rate threshold value (RTV), the magnitude threshold value (MTV), and the values and time periods actually employed in the disclosure may change, depending on such variables as material characteristics of the chemiresistor and the VOC to be detected, the type of electrodes used, location of the electrodes within the absorbent article, user preference, and any other variables affecting the indicator values and time periods used in the various tests.

When introducing elements of the present disclosure or the embodiments thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the disclosure are achieved and other advantageous results attained.

As various changes could be made in the above constructions, products, and methods without departing from the scope of the disclosure, it is intended that all matter contained in the above description and shown in the accompanying drawings shall be interpreted as illustrative and not in a limiting sense.

EXAMPLES

Example 1

Chemiresistors comprising various types of polymeric material were tested to determine the ability of the chemiresistors to detect the presence of various VOCs commonly present in urine and feces.

Chemiresistors comprising either (1) poly (ethylene-vinyl acetate) (PEVA), (2) poly(N-vinyl pyrrolidone) (PNVP), (3) polyisobutylene (PIB), or (4) polyepichlorohydrin (PECH) as the polymeric material, and carbon as the electrically-conductive material were evaluated for their ability to detect the presence of eight different VOCs (listed in Table 1), and water vapor. The chemiresistors were located on a chip (i.e., an integrated circuit package), and the chip comprising the four chemiresistors was obtained from Sandia National Laboratories (Albuquerque, N. Mex.).

25 microliters of each VOC were independently placed into separate 500 milliliter bottles, and the bottles were sealed. The compounds were warmed to about 37° C. for about 20 minutes. The bottles were then allowed to return to room temperature.

The chemiresistors were connected to an ohmmeter using standard measurement leads that ran from a particular chemiresistor on the chip to the ohmmeter, and the ohmmeter was connected to a computer by a serial port for data acquisition. The chip comprising all four chemiresistors was hung by the leads of the ohmmeter from the top of the first bottle comprising trimethylamine, and the bottle was sealed with parafilm and film pressed sealed around the leads. The chemiresistors were kept in the sealed first bottle for about 2 to 3 minutes at room temperature, and real time measurements of the resistance of the first chemiresistor (i.e., the chemiresistor connected to the leads) were recorded by the computer. After exposure to the trimethylamine, the chip comprising the chemiresistors was removed from the bottle and the trimethylamine was allowed to desorb from the chemiresistors for about 2 to 3 minutes. The chip comprising the chemiresistors was then hung by the leads of the ohmmeter from the top of the bottle comprising triethylamine, and the bottle was sealed as described above. The chemiresistors were kept in the sealed bottle for about 2 to 3 minutes at room temperature, and real time measurements of the resistance of the first chemiresistor were recorded by the computer. After exposure to the triethylamine, the chip comprising the chemiresistors was removed from the bottle and the triethylamine was allowed to desorb from the chemiresistors for about 2 to 3 minutes. This process was repeated for each additional compound, each time recording measurements of the resistance of the first chemiresistor, until the chemiresistors had been exposed to each compound listed in Table 1. The entire process was then repeated three more times, and for each time resistance measurements were made for a different chemiresistor.

The results are illustrated in FIGS. 14 to 17, which show the change in resistance when chemiresistors comprising PEVA (FIG. 14), PVNP (FIG. 15), PIB (FIG. 16), or PECH (FIG. 17) were exposed to each compound. In general, the higher the resistance value, the more sensitive the chemiresistor was to the presence of the VOC. The drops in resistance between the times the chemiresistors were exposed to one of the VOCs, seen in FIGS. 14-17, are representative of the period of time in which the VOCs were allowed to desorb from the chemiresistors. As can be seen from these results, the PEVA and PIB chemiresistors were especially sensitive to limonen and benzaldehyde, the PECH chemiresistor was especially sensitive to benzaldehyde, and the PNVP chemiresistor was sensitive to several different compounds, including trimethylamine, benzaldehyde, ammonia hydroxide, mercaptoethanol, and water vapor.

TABLE 1

Trimethylamine
Triethylamine
Limonen
Benzaldehyde
Dimethyl disulfide
Ammonia hydroxide
Mercaptoethanol
Skatole
Water (saturated vapor)

What is claimed is:

1. An absorbent article comprising:
a chemiresistor disposed across a pair of spaced-apart electrodes, the chemiresistor comprising a plurality of electrically-conductive particles and a polymeric material;
a microprocessor capable of detecting a change in an electrical property of the chemiresistor; and
a means for signaling the presence of a change in the electrical property of the chemiresistor within the absorbent article;
wherein the resistance of the chemiresistor is capable of changing when the chemiresistor is exposed to an analyte selected from the group consisting of water vapor, a volatile organic compound present in an insult, and combinations thereof, wherein the insult is selected from the group consisting of urine, menstrual fluid, feces, blood, and combinations thereof; and
wherein the polymeric material is selected from the group consisting of polyepichlorohydrin, poly(N-vinyl pyrrolidone), polyisobutylene, poly(ethylene-vinyl acetate), ethyl cellulose, poly(diphenoxyphosphazine), and combinations thereof.

2. The absorbent article of claim 1 further comprising a housing unit, wherein the housing unit comprises the microprocessor and the means for signaling the presence of a change in the electrical resistance of the chemiresistor within the absorbent article.

3. The absorbent article of claim 1 wherein the means for signaling the presence of a change in the electrical property of the chemiresistor within the absorbent article generates a signal selected from the group consisting of an auditory signal, a tactile signal, a visual signal, and combinations thereof.

4. The absorbent article of claim 1 wherein the volatile organic compound is selected from the group consisting of ammonia hydroxide, short chain (C1-C2) acids, medium length (C8-C10) aldehydes, ketones, cresol, dimethyl disulfide, trimethylamine, limonene, acetic acid, methyl benzoate, benzamide, benzaldehyde, triethylamine, and combinations thereof.

5. The absorbent article of claim 1 wherein the volatile organic compound is selected from the group consisting of skatole, mercaptans, hydrogensulfide, short chain fatty acids, methanethiol, dimethylsulfide, and combinations thereof.

6. The absorbent article of claim 1 wherein the volatile organic compound is trimethylamine.

7. The absorbent article of claim 1 wherein the chemiresistor comprises about 20 wt. % to about 60 wt. % of the electrically-conductive particles.

8. The absorbent article of claim 1 further comprising:
a liner having a body-facing surface oriented for facing a wearer when the absorbent article is worn and an absorbent-facing surface opposite the body-facing surface;
an outer cover having an absorbent-facing surface and an outer surface; and
an absorbent structure positioned between the liner and the outer cover for absorbing body exudates penetrating the liner.

9. The absorbent article of claim 8 wherein the chemiresistor is on the outer surface of the outer cover.

10. The absorbent article of claim 9 wherein the chemiresistor is covered with a coating.

11. The absorbent article of claim 8 wherein the chemiresistor is on the absorbent-facing surface of the outer cover.

12. The absorbent article of claim 1 wherein the absorbent article comprises a first chemiresistor and at least one additional chemiresistor, wherein the resistance of the first chemiresistor is capable of changing when the first chemiresistor is exposed to a volatile organic compound present in a first insult and the resistance of the at least one additional chemiresistor is capable of changing when the at least one additional chemiresistor is exposed to a volatile organic compound present in at least one additional insult, wherein the first insult and the at least one additional insult are different insults.

13. An absorbent article comprising:
a chemiresistor disposed across a pair of spaced-apart electrodes, the chemiresistor comprising a plurality of electrically-conductive particles and a polymeric material, wherein the polymeric material is selected from the group consisting of polyepichlorohydrin, poly(N-vinyl pyrrolidone), polyisobutylene, poly(ethylene-vinyl acetate), ethyl cellulose, poly(diphenoxyphosphazine), and combinations thereof;
a microprocessor capable of detecting a change in an electrical property of the chemiresistor; and
a transmitter capable of sending a signal to a receiver at a location remote from the absorbent article, the receiver comprising an insult alarm capable of signaling the presence of a change in the electrical property of the chemiresistor within the absorbent article;
wherein the resistance of the chemiresistor is capable of changing when the chemiresistor is exposed to an analyte selected from the group consisting of water vapor, a volatile organic compound present in an insult, and combinations thereof, wherein the insult is selected from the group consisting of urine, menstrual fluid, feces, blood, and combinations thereof.

14. The absorbent article of claim 13 further comprising a housing unit, wherein the housing unit comprises the microprocessor and the transmitter.

15. The absorbent article of claim 13 wherein the insult alarm generates a signal selected from the group consisting of an auditory signal, a tactile signal, a visual signal, and combinations thereof.

16. The absorbent article of claim 13 wherein the volatile organic compound is selected from the group consisting of ammonia hydroxide, short chain (C1-C2) acids, medium length (C8-C10) aldehydes, ketones, cresol, dimethyl disulfide, trimethylamine, limonene, acetic acid, methyl benzoate, benzamide, benzaldehyde, triethylamine, and combinations thereof.

17. The absorbent article of claim 13 wherein the volatile organic compound is selected from the group consisting of skatole, mercaptans, hydrogensulfide, short chain fatty acids, methanethiol, dimethylsulfide, and combinations thereof.

18. The absorbent article of claim 13 wherein the volatile organic compound is trimethylamine.

19. The absorbent article of claim 13 wherein the chemiresistor comprises about 20 wt. % to about 60 wt. % of the electrically-conductive particles.

20. The absorbent article of claim 13 further comprising:
a liner having a body-facing surface oriented for facing a wearer when the absorbent article is worn and an absorbent-facing surface opposite the body-facing surface;
an outer cover having an absorbent-facing surface and an outer surface; and
an absorbent structure positioned between the liner and the outer cover for absorbing body exudates penetrating the liner.

21. The absorbent article of claim 20 wherein the chemiresistor is on the outer surface of the outer cover.

22. The absorbent article of claim 21 wherein the chemiresistor is covered with a coating.

23. The absorbent article of claim 20 wherein the chemiresistor is on the absorbent-facing surface of the outer cover.

24. The absorbent article of claim 13 wherein the absorbent article comprises a first chemiresistor and at least one additional chemiresistor, wherein the resistance of the first chemiresistor is capable of changing when the first chemiresistor is exposed to a volatile organic compound present in a first insult and the resistance of the at least one additional chemiresistor is capable of changing when the at least one additional chemiresistor is exposed to a volatile organic compound present in at least one additional insult, wherein the first insult and the at least one additional insult are different insults.

25. A method of detecting the presence of an insult within an absorbent article, the method comprising:
providing to a wearer an absorbent article comprising a chemiresistor disposed across a pair of spaced-apart electrodes, the chemiresistor comprising a plurality of electrically-conductive particles and a polymeric material, wherein the polymeric material is selected from the group consisting of polyepichlorohydrin, poly(N-vinyl pyrrolidone), polyisobutylene, poly(ethylene-vinyl acetate), ethyl cellulose, poly(diphenoxyphosphazine), and combinations thereof;
monitoring an electrical property of the chemiresistor as the absorbent article is being worn by the wearer, wherein the resistance of the chemiresistor is capable of changing when the chemiresistor is exposed to an analyte selected from the group consisting of water vapor, a volatile organic compound present in an insult, and combinations thereof, wherein the insult is selected from the group consisting of urine, menstrual fluid, feces, blood, and combinations thereof;
determining a proportional difference in the electrical property over time and providing a difference indicator value corresponding to the determined proportional difference; and
comparing the difference indicator value to a difference threshold value to determine the presence of the insult, the water vapor, or combinations thereof, in the absorbent article.

26. The method of claim 25 further comprising communicating the presence of the insult, the water vapor, or combinations thereof, to a caregiver and/or a wearer when the difference indicator value compared to the difference threshold value is indicative of the presence of the insult, the water vapor, or combinations thereof.

27. A method of detecting the presence of an insult within an absorbent article, the method comprising:
providing to a wearer an absorbent article comprising a chemiresistor disposed across a pair of spaced-apart electrodes, the chemiresistor comprising a plurality of electrically-conductive particles and a polymeric material, wherein the polymeric material is selected from the group consisting of polyepichlorohydrin, poly(N-vinyl pyrrolidone), polyisobutylene, poly(ethylene-vinyl acetate), ethyl cellulose, poly(diphenoxyphosphazine), and combinations thereof;
monitoring an electrical property of the chemiresistor as the absorbent article is being worn by the wearer, wherein the resistance of the chemiresistor is capable of changing when the chemiresistor is exposed to an analyte selected from the group consisting of water vapor, a volatile organic compound present in an insult, and combinations thereof, wherein the insult is selected from the group consisting of urine, menstrual fluid, feces, blood, and combinations thereof;
determining a rate of change in the electrical property over time and providing a rate indicator value corresponding to the determined rate of change; and
comparing the rate indicator value to a rate threshold value to determine the presence of the insult, the water vapor, or combinations thereof, in the absorbent article.

28. The method of claim 27 further comprising communicating the presence of the insult, the water vapor, or combinations thereof, to a caregiver and/or a wearer when the rate indicator value compared to the rate threshold value is indicative of the presence of the insult, the water vapor, or combinations thereof.

* * * * *